United States Patent [19]

Kopf

[11] Patent Number: 5,049,268

[45] Date of Patent: Sep. 17, 1991

[54] FILTER PLATE, FILTER PLATE ELEMENT, AND FILTER COMPRISING SAME

[76] Inventor: Henry B. Kopf, 108 Coatbridge Cir., Cary, N.C. 27511

[21] Appl. No.: 364,616

[22] Filed: Jun. 6, 1989

Related U.S. Application Data

[63] Continuation-in-part of Ser. No. 235,046, Aug. 22, 1988, Pat. No. 4,882,050, which is a continuation-in-part of Ser. No. 104,177, Oct. 2, 1987, Pat. No. 4,867,876.

[51] Int. Cl.$^5$ .................. B01D 25/12; B01D 13/00
[52] U.S. Cl. .................. 210/231; 210/321.75; 210/321.84; 210/456
[58] Field of Search ............ 210/228, 231, 321.84, 210/321.75, 346, 433.2, 456

[56] References Cited

U.S. PATENT DOCUMENTS

| | | |
|---|---|---|
| 744,761 | 11/1903 | James . |
| 802,105 | 10/1905 | Johnson et al. . |
| 1,138,251 | 5/1915 | Schaefer . |
| 1,282,414 | 12/1918 | Hagstrom . |
| 1,540,251 | 9/1925 | Buckley et al. . |
| 2,390,628 | 12/1945 | Van Winkle .................. 210/188 |
| 2,473,986 | 9/1949 | Booth .................. 210/185 |
| 2,590,242 | 3/1952 | Fusco .................. 210/188 |
| 3,221,883 | 12/1965 | Lennström .................. 210/228 |
| 3,520,803 | 7/1970 | Iaconelli .................. 210/23 |
| 3,585,131 | 6/1971 | Esmond .................. 210/321 |
| 3,831,763 | 8/1974 | Breysse .................. 210/321.84 |
| 3,872,015 | 3/1975 | Madsen .................. 210/321.84 |
| 3,966,612 | 6/1976 | Johansson .................. 210/238 |
| 3,984,324 | 10/1976 | Wang .................. 210/321.84 |
| 3,988,242 | 10/1976 | Kurita et al. .................. 210/227 |
| 4,229,304 | 10/1980 | Fismer .................. 210/231 |
| 4,235,721 | 11/1980 | Nakamura et al. .................. 210/227 |
| 4,310,416 | 1/1982 | Tanaka et al. .................. 210/321.3 |
| 4,411,784 | 10/1983 | Esmond .................. 210/321.1 |
| 4,430,218 | 2/1984 | Perl et al. .................. 210/321.3 |
| 4,540,492 | 9/1985 | Kessler .................. 216/651 |
| 4,543,187 | 9/1985 | Steppacher .................. 210/232 |
| 4,624,784 | 11/1986 | Lefebvre .................. 210/321.1 |
| 4,735,718 | 5/1988 | Peters .................. 210/321.1 |
| 4,750,983 | 6/1988 | Foster et al. .................. 204/301 |
| 4,769,140 | 9/1988 | Van Dijk et al. .................. 210/184 |
| 4,801,381 | 1/1989 | Niesen .................. 210/321.84 |
| 4,867,876 | 9/1989 | Kopf .................. 210/228 |
| 4,882,050 | 11/1989 | Kopf .................. 210/231 |
| 4,956,085 | 9/1990 | Kopf .................. 210/231 |
| 4,980,054 | 12/1990 | Lavender .................. 210/321.84 |
| 4,997,565 | 3/1991 | Niesen .................. 210/321.84 |

FOREIGN PATENT DOCUMENTS

| | | |
|---|---|---|
| 36926 | 8/1984 | European Pat. Off. . |
| 2930986 | 2/1980 | Fed. Rep. of Germany . |
| 229603 | 1/1985 | German Democratic Rep. . |
| 8600237 | 1/1986 | PCT Int'l Appl. . |
| 1392030 | 4/1975 | United Kingdom . |

OTHER PUBLICATIONS

Prostak TM Bench Top Development System Lit No. SD281, "Toyo Soda UltraFiltration Cassette UF-LABO" Undated.
"Laboratory Ultrafiltration Products for Improved Biological Recovery" Lit No. AB841, 10188.
"Shorten the Race to the Market with Millipore Pilot and Process Systems," Lit No. SD100, 1/88.

Primary Examiner—Stanley S. Silverman
Assistant Examiner—Thomas M. Lithgow
Attorney, Agent, or Firm—Steven J. Hultquist

[57] ABSTRACT

A filter plate having a flow channel area on its main top surface, and liquid distribution and collection basins, each of polygonal shape, on its main bottom surface. Liquid inlet and discharge trough openings extend through the plate adjacent the respective distribution and collection basins, to communicate the basins on the main bottom surface of the plate with the flow channel area on the main top surface thereof. Such plates may be associated in opposedly facing pairs to form enclosed flow channels characterized by fluid flow patterns which are substantially uniform across the full transverse extent of the flow path and which facilitate the utilization of the full areal extent of the filter media employed therewith. Also described is a unitary filter element support which may be usefully employed in the filter. The filter of the invention may be advantageously employed for dewatering of aqueous biomass suspensions, desalting of proteins, removal of secreted metabolites from cellular suspensions, and the like.

6 Claims, 14 Drawing Sheets

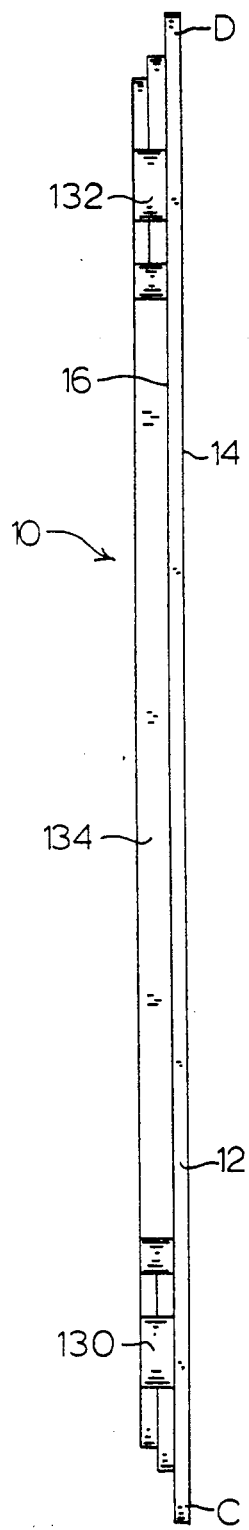
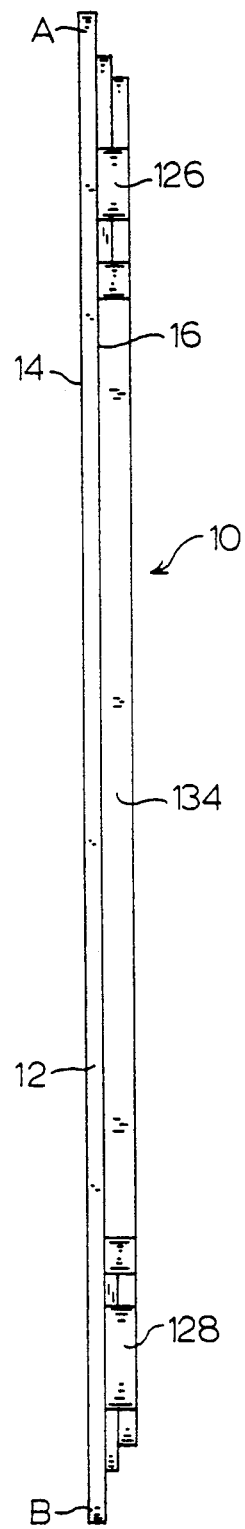
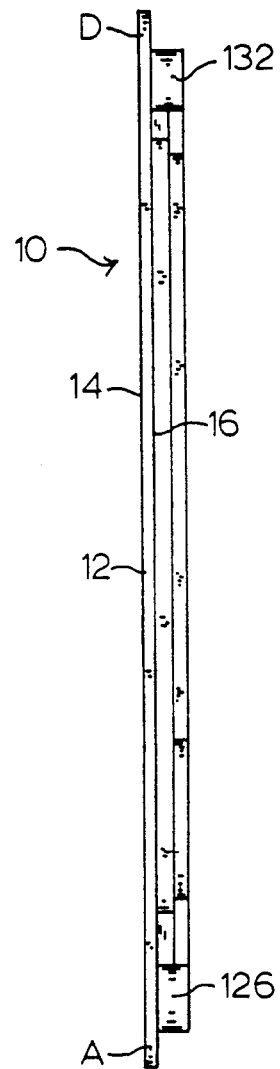
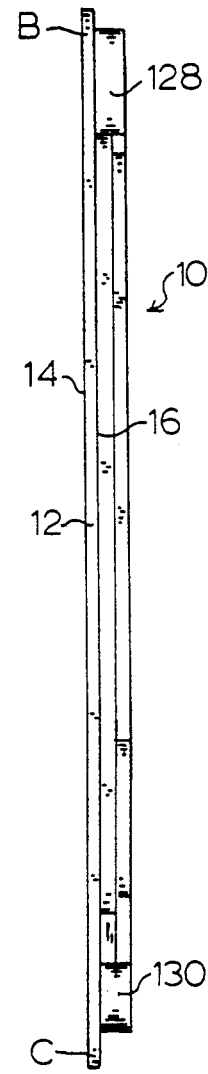
FIG. 3  FIG. 4  FIG. 5  FIG. 6

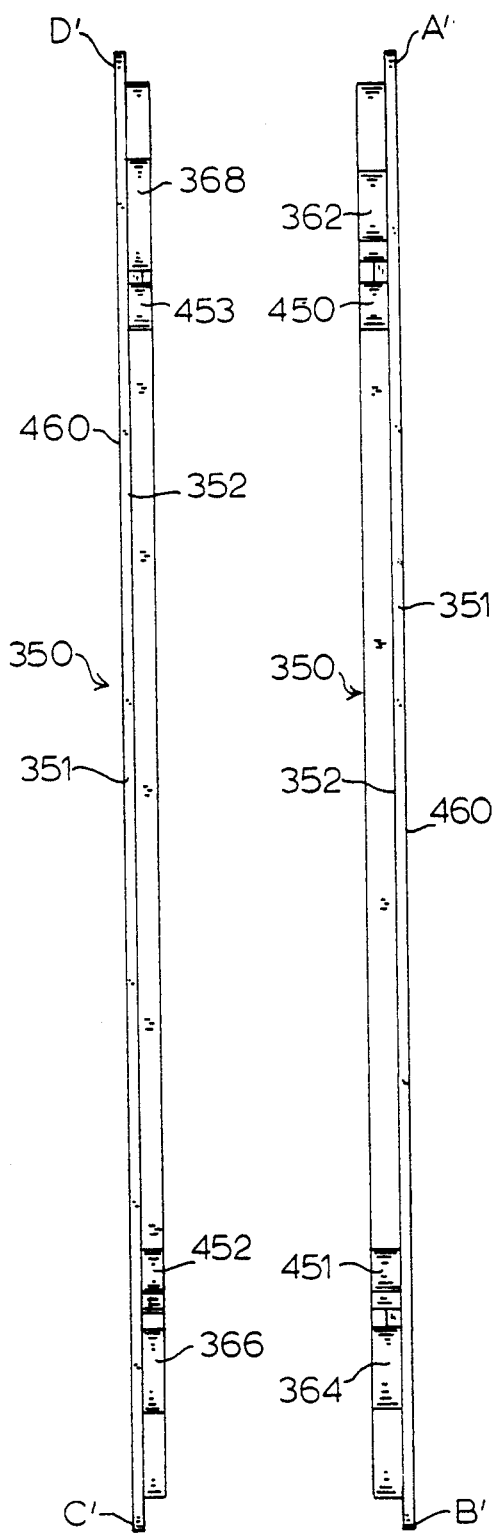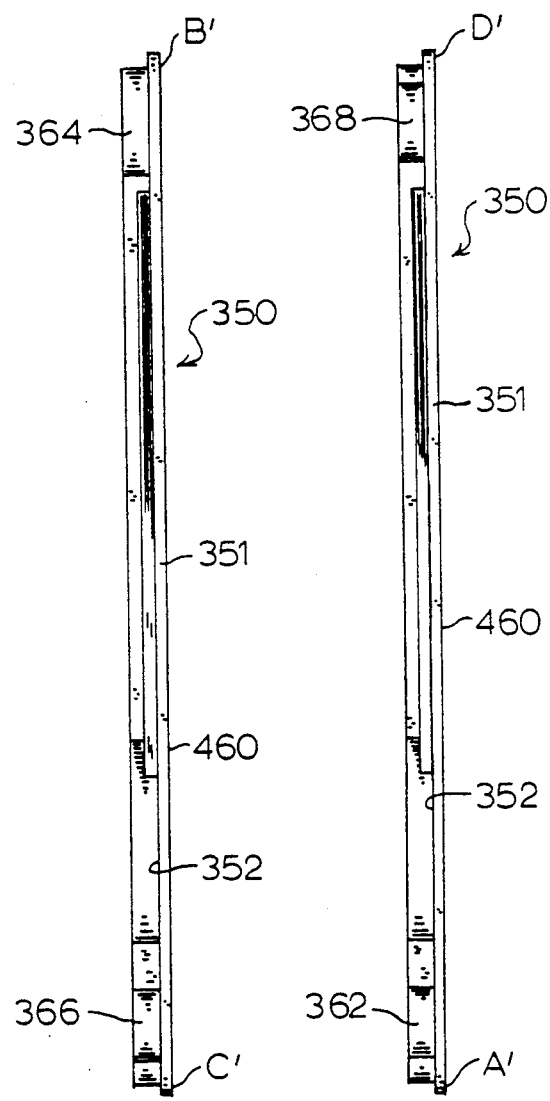
FIG. 13 FIG. 14 FIG. 15 FIG. 16

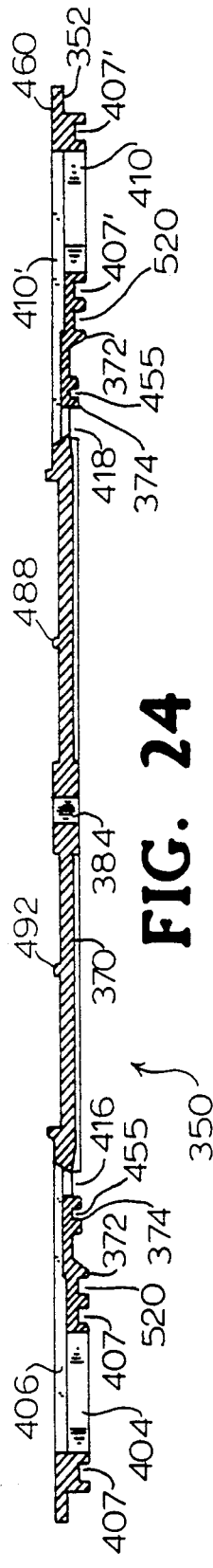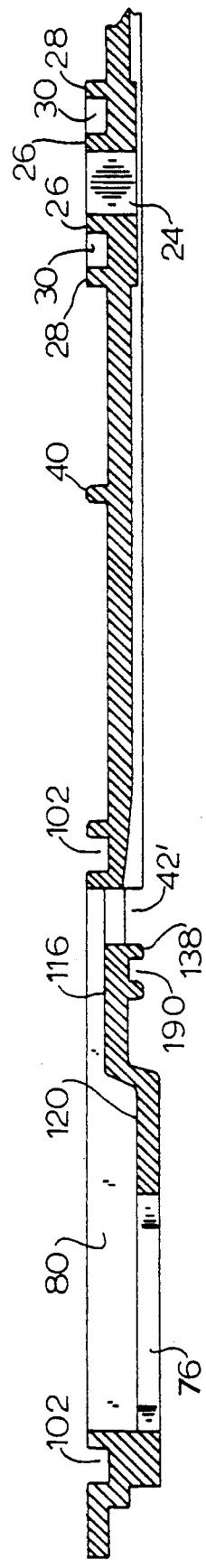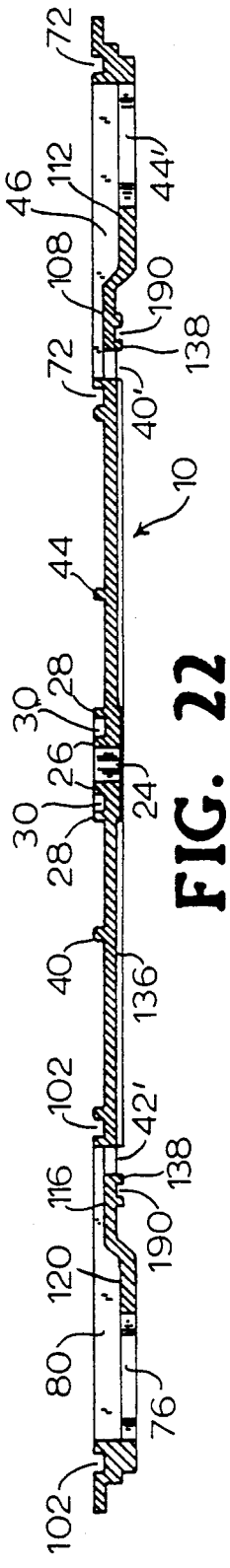

FILTER PLATE, FILTER PLATE ELEMENT, AND FILTER COMPRISING SAME

This is a continuation-in-part of U.S. application Ser. No. 07/235,046 filed Aug. 22, 1988, and issued Nov. 21, 1989 as U.S. Pat. No. 4,882,050, which in is turn a continuation-in-part of U.S. application Ser. No. 07/104,177 filed Oct. 2, 1987, and issued Sept. 19, 1989 as U.S. Pat. No. 4,867,876.

BACKGROUND OF THE INVENTION

1. Field of The Invention

This invention relates generally to cross-flow filters comprising a multiplicity of stacked filter plates, of a type wherein filter elements are disposed between adjacently paired stacked plates, and to filter plates and filter elements useful in such cross-flow filters.

2. Description of the Related Art

Stacked plate cross-flow filters are utilized in a variety of solids-liquid separation operations, including the dewatering of solids-liquid suspensions such as aqueous biomass suspensions, the desalting of proteins, and the removal of secreted metabolites from cellular cultures.

In such systems, the stacked plates making up the cross-flow filter are typically mounted in a unitary frame structure whereby the respective plates are retained in alignment, in a so-called "plate and frame" construction.

A unitary liquid feed conduit provided with openings at spaced intervals along its length and extending through the stacked plates is typically employed as a feed means from which influent solids-containing liquid is introduced into the flow channels defined between adjacent plates in the stacked plate assembly. The flow channels in the plate and frame filter contain filter elements, such as disposable filter paper sheets, with which the solids-containing liquid is contacted and through which solids-depleted liquid passes. A unitary liquid withdrawal conduit featuring openings at spaced intervals along its length extends through the stacked plates in liquid flow communication with the respective flow channels of the stacked plate assembly and conveys solids-depleted liquid out of the filter system.

As filtration proceeds, the filtered solids build up in the flow channels of the filter, on the "feed liquid sides", i.e., active filtration surfaces, of the filter sheets. The filter then is periodically backwashed, or alternatively, it may be fully shut down after a predetermined time or after a predetermined level of solids has accumulated in the flow channels on the filtration surfaces of the filter sheet elements, following which the system is drained of liquid, and the filter sheets replaced as necessary.

In one type of presently marketed stacked filter system, commercially available from Millipore Corporation (Bedford, Massachusetts) as the Prostak® crossflow filter, the adjacent filter plates define a flow channel. Solids-containing influent liquid is fed at one side of the plate from a central location into a transversely extending feed distribution conduit, which is provided with openings at spaced-apart intervals along the length of the conduit for egress of the solids-containing liquid. At the opposite side of the adjacent plates, the flow channel is similarly constructed with a liquid collection conduit having openings along its length to collect the solids-depleted liquid and discharge same from a central outlet communicating with the collection conduit.

A major problem which has been encountered in cross-flow filters of the above-described type is that the liquid flow distribution, as for example reflected by the volumetric liquid flow rate or liquid superficial velocity, is highly non-uniform in the transverse direction of the flow channel. Such maldistribution of the solids-containing liquid is a result of the fact that the influent liquid is introduced into the feed distribution conduit at a central location.

Due to the pressure drop in the transverse direction, from the medial inlet port out to the extremities of the feed distribution conduit, the local longitudinal flow (cross-flow) of liquid from the inlet side to the outlet side of the stacked plates, at progressively farther transverse distances from the central liquid inlet port, is progressively reduced to an extent which is commensurate with the pressure drop experienced as the liquid is directed transversely to the outer extremities of the distribution conduit.

As a result, there is preferential channeling of the liquid at the central part of the flow channel from the inlet side to the outlet side thereof, and concomitant under-utilization of the peripheral areas of the filter. When the solids in the central portion have been built up to a point requiring backwashing or draining of the filter, the peripheral areas of the filter still have available capacity to separate solids from the feed liquid.

Such transverse maldistribution of the feed liquid in cross-flow filters of the aforementioned type could conceivably be overcome by the provision of header manifolds to introduce feed liquid into the filtration channels at multiple introduction points along the sides of the stacked filter plates, with a corresponding outlet header manifold arrangement at the opposite side of the stacked plates. Unfortunately, however, such provision would significantly increase the overall system pressure drop as well as the complexity of the filter system, since it could be necessary to positively seal the multiplicity of feed liquid branch lines passing from the manifold into the filter.

Another type of stacked plate cross-flow filter which has been commercialized employs a transversely extending liquid distribution conduit with spaced-apart openings therein to introduce solids-containing liquid into the flow channel between adjacent stacked plates, but instead of a central inlet port to flow the solids-containing liquid to such conduit, the liquid is axially fed into the conduit from a feed line connected to a transverse extremity of the conduit. Filters of such type are available from Millipore Corporation (Bedford, Massachusetts) under the trademark Pellicon®. This feed arrangement results in a progressive diminution of the liquid pressure at increasing transverse distances from the feed end of the distribution conduit, which in turn results in progressively transversely decreased cross-flow rates of liquid in the flow channel.

In an effort to overcome the aforementioned liquid flow maldistribution characteristics of stacked plate filters, filter plates have been constructed with baffle elements defining discrete flow channels, with the intent of achieving a more uniform distribution of the solids-containing influent liquid across the full areal extent of the filter elements in the flow channels of the filter.

A filter plate commercially available from Toyo Soda Manufacturing Company, Ltd. (Tokyo, Japan) features a structure in which solids-containing influent liquid is introduced to the flow channel at a central inlet port at one side of the plate. A wall is disposed in front of the liquid inlet, extending upwardly from the floor of the flow channel and transversely toward the extremities of the flow channel, to divide the influent stream into two outwardly directed streams. Downstream from such stream-splitting wall is a longitudinally extending divider partition, the stream-splitting wall and the divider partition together forming a "T" construction when viewed in plan view. Longitudinally spaced from and parallel to the stream-splitting wall are a series of baffle partitions on either side of the divider partition. The baffles extend transversely part-way across the flow channel on either side of the divider partition, so that there is formed a serpentine flow path for each of the split streams, on the respective sides of the partition. A unitary liquid outlet port is provided at the opposite side of the stacked plates from the inlet port, whereby the respective serpentine flows are finally joined and discharged from the flow channels of the filter.

Although the dual serpentine flow path arrangement described above provides a somewhat better distribution of liquid flow across the areal extent of the filter paper element, the sharp turns in the flow path at the extremities of the baffles create edge and entrance effects in the flow streams which produce substantial dead space and bypassing therein. As a result of such anomalous flow phenomena, the filtration efficiency of the baffled serpentine flow arrangement is significantly reduced.

My prior copending U.S. Pat. application No. 07/104,177 filed Oct. 2, 1987 describes a filter plate characterized by substantially uniform transverse distribution of liquid from a unitary liquid feed port, and highly uniform liquid cross-flow across the full transverse extent of the flow channel formed when plates of such type are stacked to form a cross-flow filter.

The filter plate of this copending application has a generally planar and rectangular shape with a substantially flat bottom surface. A top surface of the plate is provided with an upwardly extending wall circumscribingly bounding a flow channel of generally rectangular shape. A liquid inlet port is disposed at a medial part of a first side of the flow channel, with the liquid outlet port at a medial part of a second side of the flow channel opposite the first side thereof. The liquid inlet port is joined in liquid flow communication with a liquid feed trough extending transversely across the first side of the flow channel, and the liquid outlet port is joined in liquid flow communication with a liquid collection trough extending transversely across the second side of the flow channel.

In this construction, a plurality of spaced-apart partitions extend upwardly from the floor of the flow channel between the liquid feed trough and the liquid collection trough. These partitions are of lesser height than the walls circumscribing the flow channel and are substantially parallel to one another, to define a series of sub-channels extending longitudinally between the liquid feed trough and the liquid collection trough. Both the liquid feed trough and the liquid collection trough are of progressively increasing depth from their respective medial portions to their marginal extremeties.

Plates of this prior copending application may be utilized in stacked pairs to form enclosed flow channels within which filtration may take place in a highly efficient manner. Specifically, a first plate of the type broadly described above is paired with a structurally identical second plate positioned in inverted relationship to the first plate, such that the respective circumscribingly bounding walls of the first and second plates are in abutting sealing contact with one another. In this stacked arrangement, a filter element support of generally rectangular shape approximating the dimensions of the flow channel is interposed between the adjacent plates, with filter sheet elements between the support and each of the respective paired filter plates.

My prior co-pending U.S. Pat. application No. 07/235,046 (U.S. Pat. No. 4,882,050) filed Aug. 22, 1988 discloses a filter plate suitable for use with filter elements to form a stacked plate filter. In the stacked plate filter, pairs of such filter plates are mated with filter elements therebetween, to form flow channels wherein solids-containing liquid may be contacted with the filter sheet elements for filtration thereof to produce solids-reduced liquid, and permeate.

The filter plate of this prior co-pending application has a generally planar shape with a substantially flat bottom surface. A top surface of the plate is provided with a first upwardly extending wall circumscribingly bounding a flow channel of generally rectangular shape.

The flow channel in this prior application design is circumscribingly bounded by a second upwardly extending wall interior to and of lesser height than the first circumscribingly bounding wall, the second wall being in spaced-relation to the outer wall along diagonally opposed L-shaped peripheral sections of the flow channel, each such L-shaped peripheral section comprising a leg extending transversely across the flow channel for a major portion of the length thereof, and a leg extending longitudinally for a portion of the longitudinal dimension of the flow channel and communicating at its extremity with an opening extending through the plate, with the portions of the periphery of the flow channel not comprising such L-shaped sections comprising ridge elements extending between the first and second circumscribingly bounding walls.

A liquid inlet port is disposed at a first side of the flow channel in this prior design, with a liquid outlet port at a second side of the flow channel opposite the first side thereof.

The liquid inlet port in this prior plate is joined in liquid flow communication with a liquid feed trough interior to the second bounding wall and extending transversely across the first side of the flow channel. The liquid outlet port is joined in liquid flow communication with a liquid collection trough interior to the second bounding wall and extending transversely across the second side of the flow channel.

A plurality of spaced-apart partitions extend upwardly from the floor of the flow channel between the liquid feed trough and the liquid collection trough. Such partitions are substantially parallel to one another to define a series of sub-channels extending longitudinally between the liquid feed trough and the liquid collection trough. These partitions preferably are of lesser height than the first (outer) wall circumscribing the flow channel and of substantially the same height as the second (inner) wall circumscribing the flow channel.

Plates of the foregoing type may be utilized in stacked pairs to form enclosed flow channels within which filtration may take place in a highly efficient manner. Specifically, a first plate of the type broadly described above may be paired with a corresponding second plate positioned in inverted relationship to the first plate, such that the respective first circumscribingly bounding walls of the first and second plates are in abutting sealing contact with one another. In such stacked arrangement, a filter element of generally rectangular shape approximating the dimensions of the flow channel is interposed between the adjacent plates, suitably with its peripheral edges reposed on the second bounding wall. Such filter element is provided with an interior flow structure, whereby permeate entering the interior of the element is conveyed to the edge portions of the element for discharge into the aformentioned L-shaped peripheral sections of the flow channel between the respective first and second bounding walls. In an illustrative aspect, the filter element may comprise a foraminous support of generally rectangular shape approximating the dimensions of the flow channel, interposed between the adjacent plates, with filter sheet elements between the foraminous support and each of the respective filter plates.

In the operation of a stacked filter plate assembly of the type disclosed in prior co-pending application No. 07/235,046 (U.S. Pat. No. 4,882,050), liquid introduced via the liquid inlet port enters the liquid feed trough and is laterally distributed from the associated portion of the feed trough to outer extremities thereof. The liquid flow is directed into the sub-channels to yield a longitudinal liquid cross-flow which is highly uniform over the full transverse extent of the flow channel, so that the full areal extent of the filter element is highly effectively utilized. As a result, the solids filtration capacity of the stacked plate assembly is substantially increased and the assembly is capable of significantly extended operation prior to regeneration of the filter, as compared to various prior art cross-flow plate and frame filters.

It is an object of the present invention to provide a filter plate of an improved type, which is simple and efficient in construction and operation.

It is another object of the invention to provide a filter element and a filter sheet support of an improved type.

It is another object of the invention to provide a filter comprising stacked filter plates of such type.

Other objects and advantages of the invention will be more fully apparent from the ensuing disclosure and appended claims.

SUMMARY OF THE INVENTION

In one aspect, the present invention relates to a filter plate, characterized by:

(a) a generally rectangular and generally planar shape with main top and bottom surfaces;

(b) a first wall extending upwardly from said main top surface and circumscribingly bounding a flow channel area of generally rectangular shape thereon;

(c) a second wall on said main top surface extending upwardly therefrom, said second wall being interior to and of lesser height than said first wall and in spaced relation to the first along diagonally opposed L-shaped peripheral sections of the flow channel area;

(d) each L-shaped peripheral section comprising a leg extending transversely across the flow channel area for a major portion of the width thereof, and a leg extending longitudinally for a portion of the length of the flow channel area and communicating at its extremity with an opening extending through the plate, with peripheral portions of the flow channel area not comprising such L-shaped sections comprising ridges extending between the first and second walls;

(e) an inlet port opening at a corner portion of the filter plate at a first end thereof, extending through the plate, interiorly positioned in a polygonal-shaped distribution basin on the main bottom surface of the plate, said distribution basin being bounded by generally linear side edges defining corners of the basin at respective intersections of the side edges;

(f) an inlet trough opening extending through said plate and transversely across a major portion of the width of said flow channel area and along a first side edge of said distribution basin, such that said liquid inlet trough opening communicates said distribution basin on the main bottom surface of the plate with said flow channel area on the main top surface of the plate;

(g) an outlet port opening at a corner portion of said plate diagonally opposite said inlet port opening, said outlet port opening extending through the plate, interiorly positioned in a polygonal-shaped collection basin on the main bottom surface of the plate, said collection basin being bounded by generally linear side edges defining corners of the collection basin at respective intersections of the side edges thereof;

(h) an outlet trough opening extending through the plate and transversely across a major portion of the width of said flow channel area and along a first side edge of said collection basin, such that said outlet trough opening communicates said collection basin on th main bottom surface of the plate with said flow channel area on the main top surface of the plate; and (i) a plurality of transversely spaced-apart partitions extending upwardly from the floor of the flow channel area between the liquid feed trough and the liquid collection trough, said partitions being of substantially the same height as the second wall and substantially parallel to one another to define a series of channels between the partitions, extending longitudinally between the liquid feed trough and the liquid collection trough.

In one specific embodiment, the liquid distribution basin and liquid collection basin each have quadrilateral shape, wherein each basin comprises:

said port opening port being disposed at a first said corner and the side edges intersecting at said first corner defining a first included angle w therebetween of from about 60° to about 110°;

a second corner diagonally opposite said first corner, and the side edges intersecting at said second corner defining a second included angle x therebetween of from about 45° to about 90°;

a third corner transversely adjacent said first corner and longitudinally adjacent said second corner, with the side edges intersecting at said third corner defining a third included angle y therebetween of from about 70° to about 135°;

a fourth corner longitudinally adjacent said first corner and transversely adjacent said third corner, with the side edges intersecting at said fourth corner defining a fourth angle z therebetween of from about 60° to about 90°; and the side edge extending transversely between said second and fourth corners also bounding the associated trough opening extending through said plate and communicating said basin with said flow channel area.

In another aspect, the filter plate of the invention may comprise triangular-shaped liquid distribution and liquid collection basins at respective ends of the filter plate. Each such basin includes a transversely extending side edge bounding the associated liquid trough opening extending through the plate and communicating the basin with the flow channel area. In this arrangement, the basins are bounded by substantially linear side edges defining corners of the basin at respective intersections of the side edges. In this arrangement, each basin comprises:

the liquid port opening being disposed at a first said corner and the side edges intersecting at said first corner defining a first included angle a therebetween of from about 60° to about 120°;

a second corner adjacent the associated liquid trough opening and the side edges intersecting at said second corner defining an included angle b therebetween of from about 15° to about 45°;

a third corner transversely opposite said second corner, with the side edges intersecting at said third corner defining an included angle c therebetween of from about 45° to about 75°;

In another aspect, the present invention relates to a filter element support of generally planar and non-perforate character, with diagonally opposed, longitudinally extending marginal flanges. The filter element support has main top and bottom surfaces, characterized by a series of transversely space apart ridges which extend longitudinally of the support along its full longitudinal extent, and with the transverse margins of the filter element support being devoid of such ridges.

Another aspect of the present invention relates to a filter element assembly including a filter element support as described above, with filter sheets reposed on its main top and bottom surfaces.

Further aspect of the invention relates to a stacked plate filter comprising filter plates of the type described above, provided in invertedly positioned symmetrical facing pairs, wherein each pair of filter plates forms an enclosed liquid flow channel, with a filter element disposed in each flow channel.

Other aspects and features of the present invention will be more fully apparent from the ensuing disclosure and appended claims.

BRIEF DESCRIPTION OF THE DRAWINGS

FIG. 3 is a side elevation view of the filter plate of FIGS. 1 and 2, taken along line 3—3 of FIG. 2.

FIG. 4 is a side elevation view of the filter plate shown in FIGS. 1 and 2, along line 4—4 of FIG. 2.

FIG. 5 is an edge elevation view of the filter plate of FIGS. 1 and 2, taken along line 5—5 of FIG. 2.

FIG. 6 is a side elevation of the filter plate of FIGS. 1 and 2, taken along line 6—6 of FIG. 2.

FIG. 13 is a side elevation view of the plate shown in FIGS. 11 and 12, taken along line 13—13 of FIG. 11.

FIG. 14 is a side elevation view of the plate of FIGS. 11 and 12, taken along line 14—14 of FIG. 11.

FIG. 15 is an edge elevation view of the filter plate of FIGS. 11 and 12, taken along line 15—15 of FIG. 11.

FIG. 16 is an edge elevation view of the filter plate of FIGS. 11 and 12, taken along line 16—16 of FIG. 11.

FIG. 22 is a sectional elevation view of the FIG. 1 plate, taken along line 22—22 thereof.

FIG. 23 is an enlarged sectional elevation view of a portion of the plate shown in FIG. 22.

FIG. 24 is a sectional elevation view of the FIG. 12 filter plate, taken along line 24—24 thereof.

DETAILED DESCRIPTION OF THE INVENTION, AND PREFERRED EMBODIMENTS THEREOF

The filter plate of the present invention is suitably adapted to be employed in mated pairs to form a stacked plate filter assembly in which adjacent paired plates are generally symmetrical to one another and are oriented invertedly, i.e., in opposed face-to-face relationship with respect to one another. Thus, the plates preferably are of two structural configurations which are mirror images of one another and are mated with one another in alternating fashion to form the sequential plate pairs in the stacked plate filter assembly.

The filter plates, and the interposed filter element support employed therewith, may be formed of any suitable materials of construction, including, for example, polymers such as polypropylene, polyethylene, polysulfone, polyimide, polyvinylchloride, etc; regenerated cellulose, polycarbonate, cellulose acetate, cellulose triacetate, cellulose nitrate, mixted esters of cellulose, etc.; ceramics, e.g., oxides of silicon, zirconium, and/or aluminum; metals such as stainless steel; polymeric fluorocarbons such as polytetrafluoroethylene; and compatible alloys, mixtures and composites of such materials.

Preferably, the filter plates and interposed filter element support are made of materials which are adapted to accommodate high temperatures, and chemical sterilants so that the interior surfaces of the filter may be steam sterilized and/or chemically sanitized for regeneration and reuse, as "steam-in-place" and "sterilized in situ" structures. Steam sterilization typically may be carried out at temperatures on the order of from about 121° C. to about 130° C., at steam pressures of 15-30 psi, and at a sterilization exposure time typically on the order of from about 15 minutes to about 2 hours, or even longer.

Figure 1:
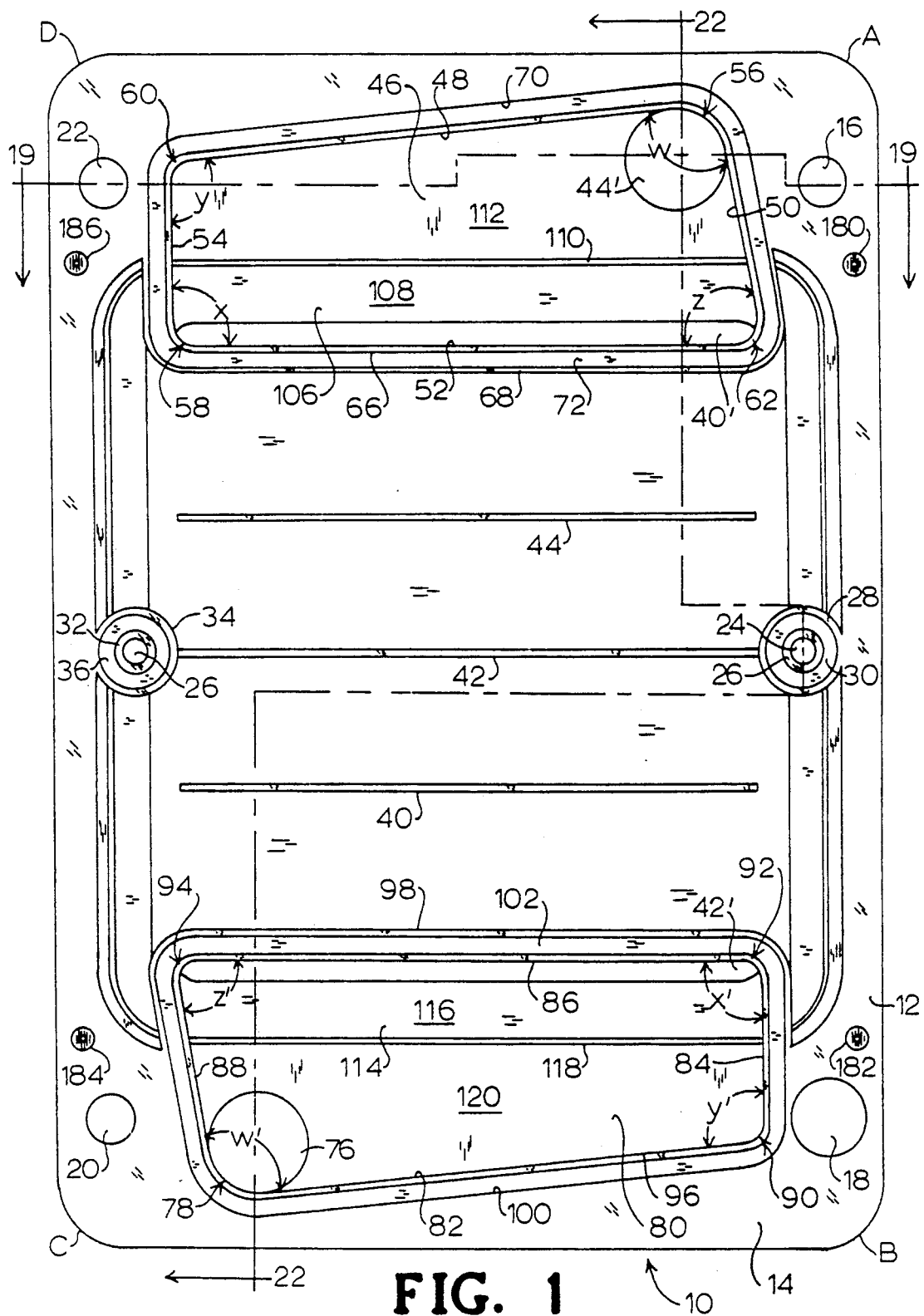
FIG. 1 is a top plan view of a filter plate according to one embodiment of the present invention.
Figure 2:
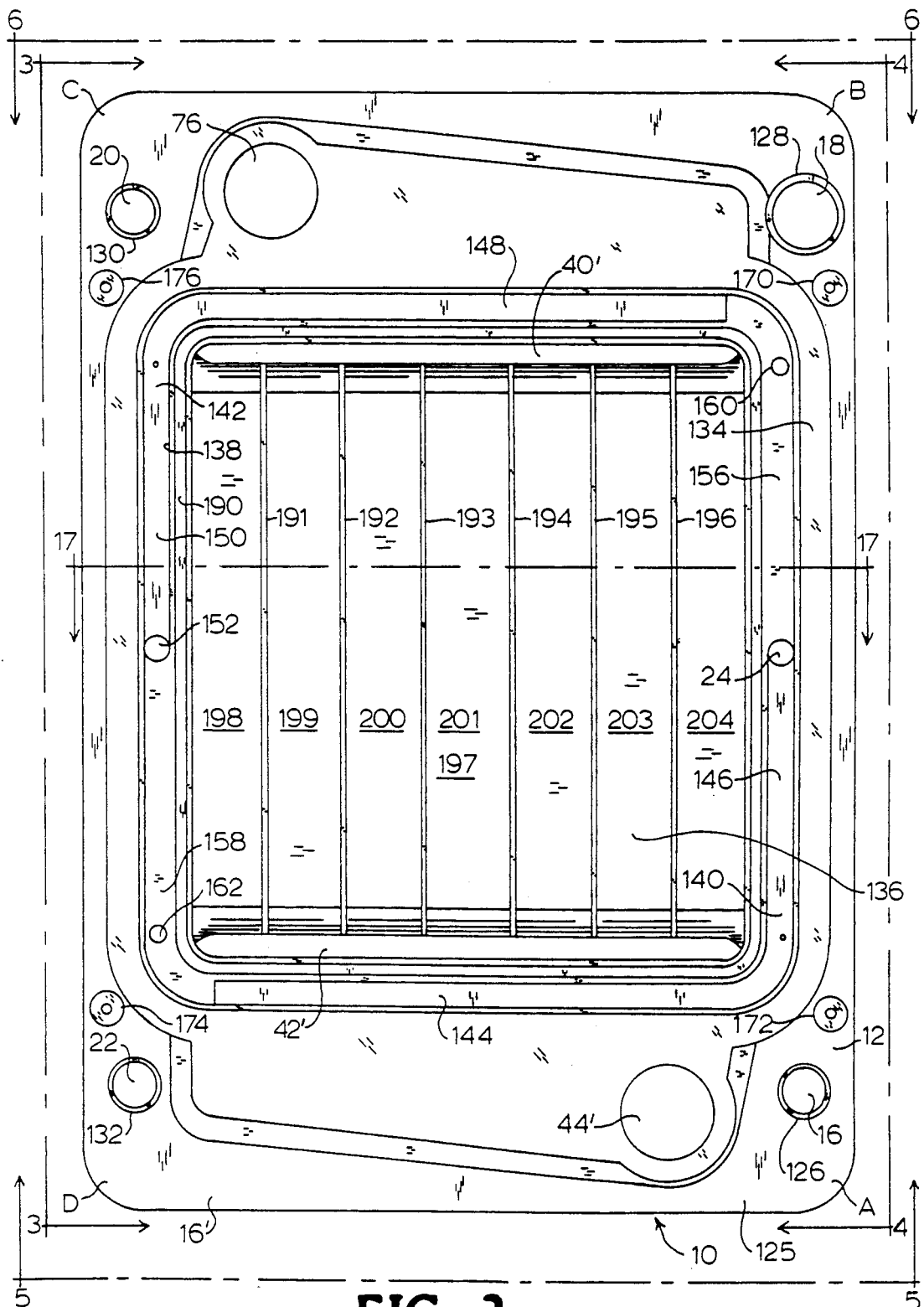
FIG. 2 is a bottom plan view of the filter plate shown in FIG. 1.

FIG. 1 is a top plan view of a filter plate 10 according to one embodiment of the present invention. The filter plate 10 comprises a main plate body 12 of generally rectangular and generally planar shape, with a main top surface 14, and a main bottom surface 16 as shown in FIG. 2, which is a bottom plan view of the same filter plate.

For ease of description in the ensuing discussion, the respective corners of the filter plate as shown in FIG. 1 are lettered consecutively, beginning at the upper right-hand corner A as shown and, proceeding clock-wise, including lower right-hand corner B, lower left-hand corner C, and upper left-hand corner D.

In the vicinity of these consecutive corners A, B, C, and D, of the filter plate are provided openings 16, 18, 20, and 22, respectively, which extend through the plate and are employed for mounting of the plate on rods of diameter closely approximating but slightly smaller than the respective openings. In this respect, it is to be noted that opening 18 is of larger size (diameter) than the remaining openings 16, 20, and 22. The purpose of such disparity in opening size is to provide a "keying" feature whereby the proper alignment of the plate is secured, since only opening 18 will fit over a large-sized rod of corresponding diameter, whereas openings 16, 20, and 22 will not accommodate passage over such a large-sized rod.

Other features or structure may be employed for the same purpose, viz., of keying the plate to a predetermined proper orientation, in place of the different sized opening 18 relative to the remaining same-sized corner openings 16, 20, and 22. For example, one of the respective corner openings may be of a different shape than the others, e.g., square or triangular in cross-section, rather than circular.

The filter plate 10 also is provided at its respective side margins, at the mid-section of the longitudinally extending plate, with openings 24 and 26 extending through the plate. These openings may be employed for egress of permeate produced in the filtration operation when the plate is deployed in a stacked plate filter assembly, and/or otherwise for accommodating ingress/egress of a selected fluid, such as steam or other sterilant fluid for effecting cleaning and regeneration of the filter, or a secondary fluid for mass transfer contacting with a primary fluid passed through the filter.

Opening 24 is circumscribed by a first collar 26 which in turn is circumscribed by a concentric second collar 28, defining an annular space 30 therebetween. The annular space 30 accommodates positioning therein of an O-ring (not shown) such as is desirably employed to effect sealing between adjacent filter plates, when the filter plate shown in FIG. 1 is utilized as a constituent part of a stacked plate filter assembly.

Opening 26 similarly is concentrically circumscribed by a smaller diameter inner collar 32 and a larger diameter outer collar 34, defining an annular space 36 therebetween, in which an O-ring (not shown) or other sealing element can be disposed.

Extending transversely across the mid-section of the plate 10 is a series of longitudinally spaced-apart, and parallelly aligned, transverse ribs 40, 42, and 44. The purpose of these ribs is to stiffen the plate so as to impart strength and enhanced structural integrity thereto.

Extending through the plate at the upper portion thereof, as shown, is a transversely extending liquid inlet trough opening 40. Correspondingly, a liquid collection trough opening 42 is provided at a lower portion of the filter plate, as shown, extending transversely across the plate.

At the upper right-hand corner portion of the filter plate shown in FIG. 1, in proximity to corner A, there is provided a liquid inlet port 44 extending through the plate and communicating with a quadrilateral-shaped feed distribution basin 46. The feed distribution basin is configured as a depression in the main top surface 12 of the plate.

The feed distribution basin 46 is bounded by generally linear side edges 48, 50, 52, and 54. These side edges at their respective intersections define corners of the quadrilateral-shaped basin, with the inlet port opening 44 disposed at a first such corner 56 and the side edges 48 and 50 intersecting at the first corner 56 defining an obtuse included angle w therebetween. A second corner 58 is diagonally opposite the first corner 56 and the side edges 52 and 54 intersecting at the second corner 58 define a substantially right (90°) included angle x therebetween.

A third corner 60 is transversely adjacent the first corner 56 and longitudinally adjacent the second corner 58. The side edges 48 and 54 intersecting at the third corner 60 define an obtuse included angle y therebetween. A fourth corner 62 is longitudinally adjacent the first corner 56 and transversely adjacent the second corner 58, with the side edges 50 and 52 intersecting at the fourth corner 62 defining an acute included angle z therebetween.

Surrounding the feed distribution basin 46, and including the bounding side edges 48, 50, 52 and 54, is a circumscribing wall 66. The circumscribing wall 66 over the lower portion of the basin as shown in FIG. 1 is in spaced relationship to a correspondingly configured outer wall 68, and the circumscribing wall 66 over its remaining upper portion is in spaced relationship to bounding edge 70 which is of corresponding configuration to the circumscribing wall 66. By such arrangement, a groove 72 is provided about the perimeter of the feed distribution basin 46, between the circumscribing wall 66 on the one hand, and bounding wall 68 and edge surface 70 on the other hand. Into the circumscribing groove 72 may be inserted a suitable sealing ring or gasket element (not shown), to seal the liquid distribution basin 46 against the main bottom surface of an adjacent plate superposed on the filter plate shown in FIG. 1 as part of a stacked plate filter assembly.

In like manner, there is provided at the lower portion of the plate as shown in FIG. 1 a liquid discharge port opening 76 extending through the plate and disposed at a first corner 78 of a quadrilateral-shaped collection basin 80, which is configured as a depression in the main top surface 12 of the plate.

The collection basin 80 is bounded by generally linear side edges 82, 84, 86 and 88, defining at their respective intersections with one another the respective corners 78, 90, 92 and 94.

Thus, analogous to the structure of the feed distribution basin 46 previously described, the collection basin 80 features included angles defined at the respective corners of the basin, including obtuse angle w' at corner 78, obtuse angle y' at corner 90, substantially right angle x' at corner 92, and acute angle z' at corner 94.

The collection basin 80 is circumscribed by bounding wall 96, which is in spaced relationship to wall 98 and edge surface 100, to form a circumscribing groove 102 about the periphery of the liquid collection basin, accommodating insertion therein of a gasket or other sealing element, to seal the liquid collection basin against the bottom surface of a filter plate superposed on the top surface of the filter plate shown in FIG. 1.

The feed distribution basin 46 comprises a transversely extending step 106 adjacent the liquid inlet trough opening 40. The step 106 comprises a flat main top surface 108 and a transition section 110 sloping downwardly from the top surface 108 to a lower main floor 112 of the basin 46.

Correspondingly, the collection basin 80 includes a step 114 comprising a main flat top surface 116 and a transition surface 118 sloping downwardly from the top surface 116 to a lower main floor 120 of the basin.

FIG. 2 is a plan view of the filter plate 10 of FIG. 1, and thus shows the details of construction the main surface 125 which is on the other side of the filter plate from the main surface 12 shown in FIG. 1.

In the FIG. 2 drawing, all parts and features previously described in connection with FIG. 1 and shown in the FIG. 2 plan view have been correspondingly numbered with respect to FIG. 1. For ease of reference in the ensuing discussion of FIG. 2, the main surface 125 of the plate will be referred to as the main top surface and other elevations of the plate as shown in FIG. 2 will be described consistently therewith, it being recognized that the relative orientations and directions FIGS. 1 and 2 are of course opposite to one another, so that for example the top main surface as described in FIG. 2 is actually the bottom surface of the plate a shown in FIG. 1.

As shown in FIG. 2, the successive rod alignment openings 16, 18, 20, and 22 extending through the plate are circumferentially bounded by respective collars 126, 128, 130, and 132, which extend upwardly from the main top surface 125 of the plate 10.

On the main top surface 125 of the plate as shown in FIG. 2, a first upwardly extending wall 134 circumscribingly bounds a flow channel area 136 of generally rectangular shape. A second upwardly extending wall 138 is provided on the main top surface of the plate, which is interior to and of lesser height than the first wall 134. The second wall 138 is in spaced relation to the first wall 134 along diagonally opposed L-shaped peripheral sections 140 and 142 of the flow channel area 136.

L-shaped peripheral section 140 comprises a leg 144 extending transversely across the flow channel area for a major portion of the width (transverse extent) thereof, and a leg 146 extending longitudinally for a portion of the length of the flow channel area and communicating at its extremity with the opening 24 extending through the plate.

In like manner, L-shaped peripheral section 142 comprises a leg 148 extending transversely across the flow channel area for a major portion of the width thereof, and a leg 150 extending longitudinally for a portion of the length of the flow channel area and communicating at its extremity with the opening 152 extending through the plate.

The peripheral portions 156 and 158 of the flow channel area 136 not comprising such L-shaped sections 140 and 142, comprise ridges 156 and 158 extending between the inner wall 138 and outer wall 134 circumscribing the flow channel area.

In the inner circumscribing wall 138 bounding the flow channel area, there is provided a groove 190 accommodating the insertion thereinto of a suitable sealing gasket, for purposes of sealing the flow channel area 136 of the plate against an interposed filter element support, as hereinafter more fully described, which is interposed between oppositely facing stacked plates when the plate shown in FIG. 2 is employed as part of a stacked plate filter.

In the diagonally opposed ridges 156 and 158 in the plate are provided depressions 160 and 162, respectively. The purpose of such depressions is to serve as keying devices for the proper registration of the plate with the filter element support employed therewith, as will be described more fully hereinafter.

At the respective corner portions of the plate are provided plate registration elements comprising locator pins 170, 172, 174, and 176. The purpose of such locator pins is to correctly align oppositely facing plates with one another, when the plate shown in FIG. 2 is employed in a stacked plate filter array.

As shown, the flow channel area features a plurality of transversely spaced-apart partitions 191, 192, 193, 194, 195, and 196. These partitions extend longitudinally along the flow channel area of the plate, extending upwardly from the floor 197 of the flow channel area between the feed trough 40 and the collection trough 42. The partitions are of substantially the same height as the bounding wall 138 circumscribing the flow channel area, and the partitions are substantially parallel to one another to define a series of channels 198, 199, 200, 201, 202, 203, and 204. The channels thus are bounded by the longitudinally extending partitions and themselves extend longitudinally between the feed trough and the collection trough.

The floor 197 of the flow channel area 136 in the vincinity of the inlet trough 40 and collection trough 42 may be slopingly downwardly configured at the intersection of the plate with the respective trough openings, to provide good flow characteristics with an absence of entrance and exit effects in the fluid streams at such regions.

FIG. 3 is a side elevation view of the filter plate 10 of FIGS. 1 and 2, taken along line 3—3 of FIG. 2. For ease of reference, the elements and features of FIG. 3 have been numbered correspondingly with respect to FIGS. 1 and 2.

FIG. 4 is a side elevation view of the filter plate 10 shown in FIGS. 1 and 2, taken along line 4—4 of FIG. 2, and correspondingly numbered with respect to FIGS. 1-3.

FIG. 5 is an edge elevation view of the filter plate of FIGS. 1 and 2, taken along line 5—5 of FIG. 2. FIG. 6 is a side elevation view of the opposite end of the filter plate of FIGS. 1 and 2, taken along line 6—6 of FIG. 2. In these respective views, the elements and features of the plate are numbered correspondingly with respect to the same elements and features in FIGS. 1-4.

FIGS. 7-10 show a filter element support according to one embodiment of the present invention, of a type which may be usefully employed with opposingly mated, paired filter plates of the type shown and described with reference to FIGS. 1-6 hereof.

Figure 7:
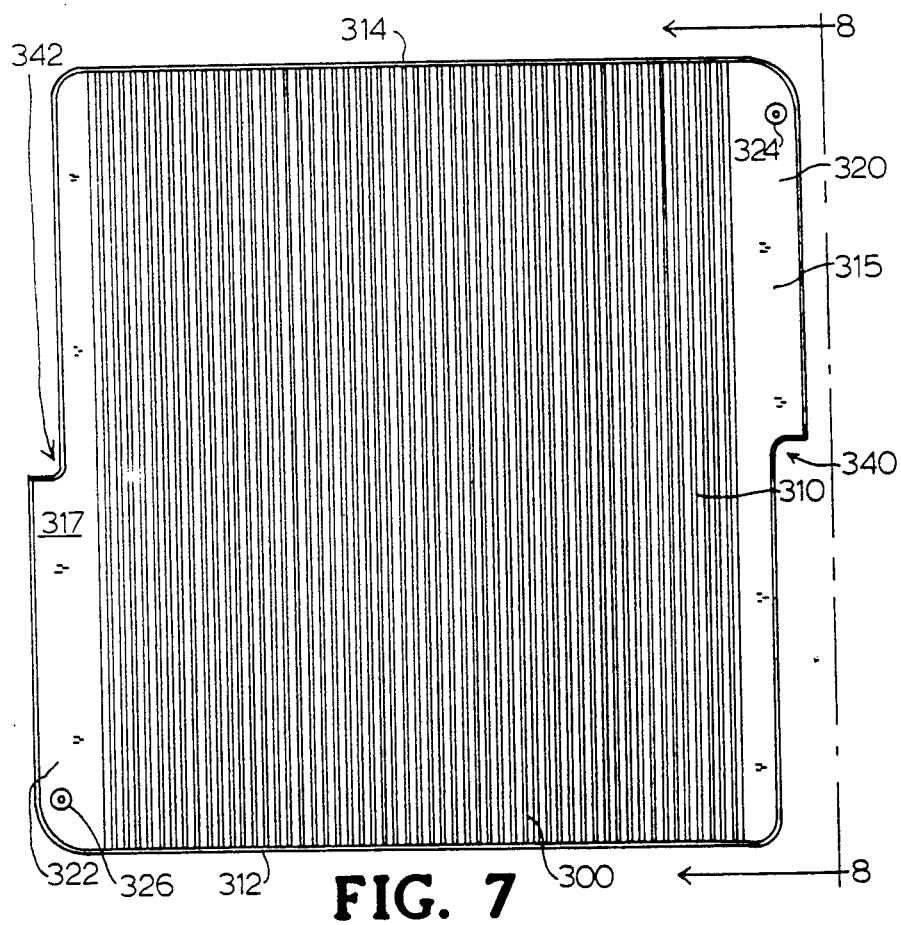
FIG. 7 is a top plan view of a filter element support according to one embodiment of the present.
Figure 8:
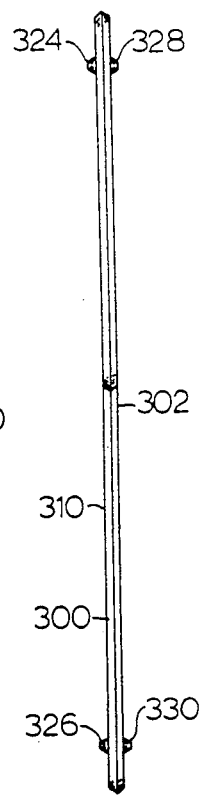
FIG. 8 is a side elevation view of the FIG. 7 filter element support, taken along line 8—8 of FIG. 7.

FIG. 7 is a top plan view of a filter element support 300, FIG. 8 being a corresponding side elevation view, taken along line 8—8 of FIG. 7.

Figure 9:
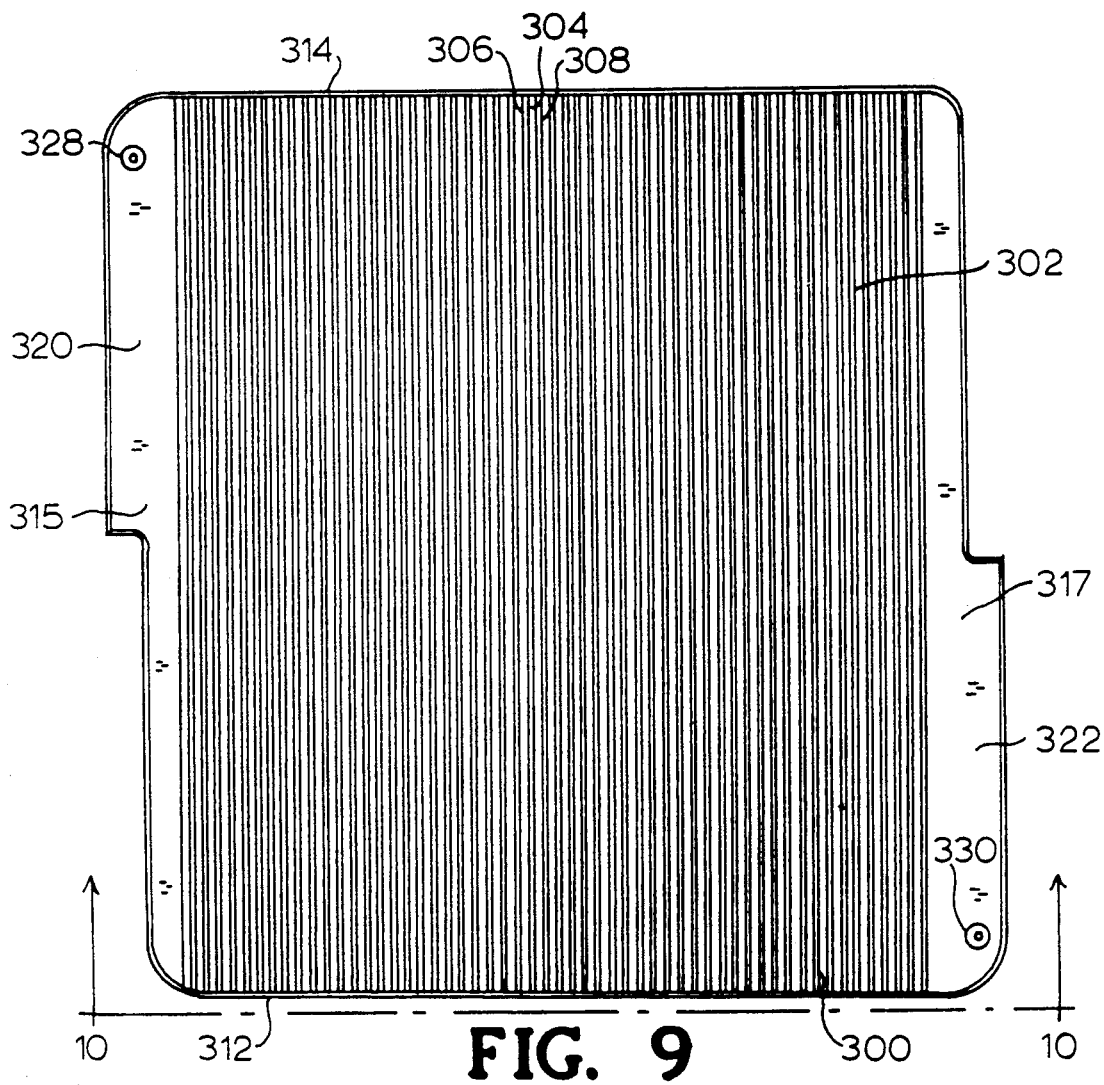
FIG. 9 is a bottom plan view of the filter element support of FIGS. 7 and 8.
Figure 10:
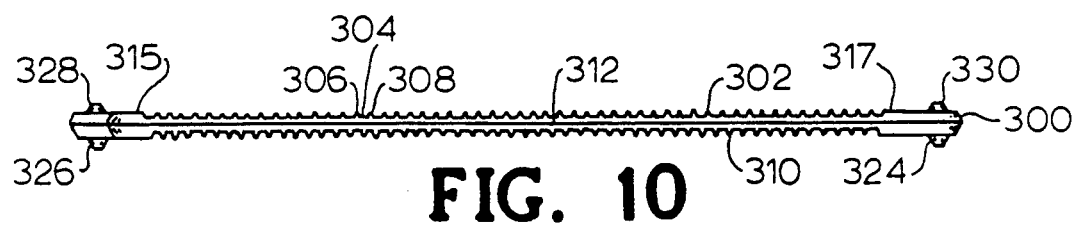
FIG. 10 is an edge elevation view of the filter element support of FIGS. 7-9, taken along line 10—10 of FIG. 9.

FIG. 9 is a bottom plan view of the filter element support 300 of FIGS. 7 and 8, and FIG. 10 is an edge elevation view of the filter element support, taken along line 10—10 of FIG. 9.

As shown in FIGS. 7-10, the filter element support 300 has a main top surface 310, on the major central portion of which is provided a series of grooves 304 and adjacent ridges 306 and 308 extending longitudinally of the support. The bottom main surface 302 of the plate (see FIG. 9) is similarly configured with a pattern of alternating crests and grooves extending longitudinally of the support from one end edge 312 to the opposite end edge 314.

On the transversely opposite, longitudinally extending side margins 315 and 317, the plate is devoid of ridges and grooves, being smooth surfaced.

Diagonally opposite one another on the longitudinally extending side margins of the support are transversely outwardly extending flange segments 320 (on margin 315) and flange segment 322 (on margin 317).

On diagonally opposite corners of the respective transversely extending flanges 320 and 322 are protrusions 324 and 326, on the top surface 310. On bottom surface 302 (see FIG. 9), corresponding keying projections 328 and 330 are provided at diagonally opposite corners of the support, on the respective transversely extending flanges 320 and 322. The protrusions on the respective flanges on opposite sides of the plate are in alignment with one another, as shown in the side elevation view of FIG. 8 and the edge elevation view of FIG. 10.

By means of the above-described flange and protrusion structure of the filter element support, the support is cooperatively matable with filter plates of the invention, of the type shown in FIGS. 1-6. Referring to the plate as shown in FIG. 2, the filter element support may be reposed on the FIG. 2 plate, such that the protrusion element 328 is reposed in depression 160 of the plate ridge 156, and correspondingly the protrusion element 330 is reposed in the depression 162 on plate ridge 158. By such mating, the transversely extending flanges repose on the diagonally opposed ridges of the plate, so that the "cut-away" portions 340 and 342 of the support overlie the longitudinally extending legs 146 and 150 of the diagonally opposite L-shaped peripheral sections of the flow channel area, in order that such sections are unoccluded by the filter element support.

The filter element support shown in FIGS. 7-10 may be suitably employed to provide a filter element for the stacked plate filter of the present invention, by mating suitable sheets of filter medium (not shown) with the respective top and bottom main surfaces 310 and 302 of the filter element support.

Such filter sheets are coextensive in areal extent with the grooved portion of the support, so that each respective filter sheet is supportably reposed on the crests (ridges) 306 and 308 on the respective top and bottom main surfaces of the plate. Accordingly, fluid permeating through the filter sheets will pass into the respective grooved passages between the filter sheet and support and flow longitudinally to an adjacent edge (312, 314) of the plate and into the L-shaped peripheral sections of the flow channel area defined by opposedly facing filter plates between which the support is disposed.

Preferably, the filter sheets are fully coextensive in areal extent with the support, having side marginal extremities which are reposed on the transverse side margins 315 and 317 of the support. For this purpose, the sheets of correspondingly configured filter media are provided with diagonally opposite openings to accommodate the protrusion elements 324, 326, 328, and 330.

Although the respective filter sheets may simply be "sandwiched" with the filter element support therebetween in a non-bonded fashion, so that the respective filter sheets are held in place only by frictional forces and by the compression forces of the respective bearing surfaces of the filter plates on the support, it generally is preferred to secure the filter sheets to the respective top and bottom surfaces of the filter plate, to provide a unitary filter element.

For this purpose, any method or means of securement may suitably be employed, as for example including ultrasonic bonding, adhesive bonding, solvent welding, mechanical fastening, etc.

The respective filter sheets may be paper filter sheets, comprising a non-woven web of cellulosic fibers, or any other filtration medium commonly employed in sheet form which is readily cut or otherwise shaped to the form required for the filter of the present invention. A particularly advantageous filter sheet in filter systems of the type envisioned by the present invention are polysulfone filter sheets, which are readily commercially available.

It will be recognized that the keying projections 324, 326, 328, and 330 are optional features in the support structure, and may suitably be omitted, if desired. Nonetheless, such keying feature provides a positive locking of the filter element support to the associated plates which are mated with one another and enclose the filter element support. Further, while the protrusions which have been illustratively shown are frustonical elements, it will be recognized that any suitable shapes or configurations of keying elements may be employed, within the broad practice of the invention.

Figure 11:
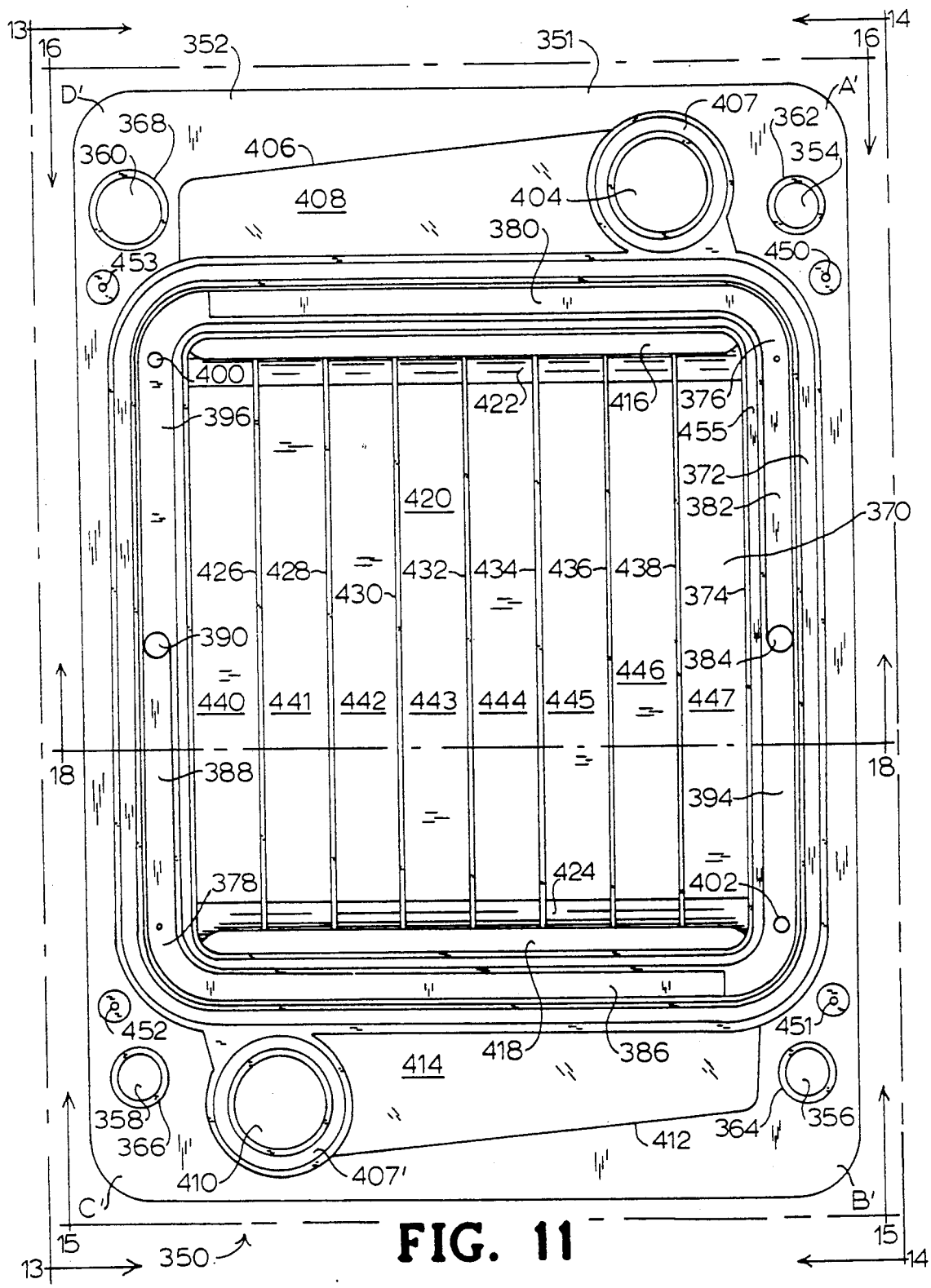
FIG. 11 is a top plan view of a filter plate according to another embodiment of the present invention, which is symmetrically formed with respect to the plate illustrated in FIGS. 1-6, and adapted to cooperatively mate therewith in inverted facing relationship.

FIG. 11 is a top plan view of a filter plate 350 according to another embodiment of the present invention, which is symmetrically formed with respect to the plate illustrated in FIGS. 1-6, and adapted to be cooperatively mated therewith in inverted facing relationship. In other words, the face of the previously described plate which is shown in FIG. 2 is symmetrically formed to mate in opposed facing relationship with the main top surface 352 of plate 350.

The plate shown in FIG. 11 is correspondingly labeled wide corners A', B', C', and D' and is provided with corner openings 354, 356, 358, and 360, with opening 360 being of larger size than the other, same diameter openings, to facilitate registration in the mounting of the plates in a stacked assembly, as previously described. Rod opening 354 is circumscribed by a collar 362 extending upwardly from the main plate body 351. Similarly, opening 356 is circumscribed by collar 364, opening 358 is circumscribed by collar 366, and opening 360 is circumscribed by collar 368.

The central flow channel area 370 of the plate is circumscribed by an outer wall 372 extending upwardly from the main top surface 352 of the plate.

Interior to the outer wall 372 is an inner wall 374 of lesser height than outer wall 372 and in spaced relation to the outer wall along diagonally opposed L-shaped peripheral sections 376 and 378 of the flow channel area.

L-shaped peripheral section 376 comprises a leg 380 extending transversely across the flow channel area for a major portion of the width thereof, and a leg 382 extending longitudinally for a portion of length of the flow channel area and communicating at its extremity with an opening 384 extending through the plate. In like manner, the L-shaped peripheral section 378 comprises a transverse leg 386, and a longitudinally extending leg 388 terminating in plate opening 390. Each of the L-shaped peripheral sections defines a channel between the first and second walls, such as may be employed for egress of filtrate from the plate, through the respective plate openings 384 and 390.

The peripheral portions of the flow channel area not comprising the L-shaped sections, comprise ridges 394 and 396, extending from the inner wall 374 to the outer wall 372. In these ridges are provided depressions 400 and 402 for keying the mating of a filter element support (of the type shown in FIGS. 7–10 hereof) with the plate.

At a corner region of the plate in proximity to corner A' is provided a liquid port opening 404 extending through the plate and communicating with quadrilateral-shaped basin 406 on the opposite side of the plate, surface 408 of the plate being raised relative to the main plate body 351.

Correspondingly, a liquid port opening 410 is provided at a diagonally opposite corner region of the plate proximate to corner C', and such liquid port opening extends through the plate and communicates on the opposite side of the plate with the collection basin 412 whose floor defines the raised surface 414 of the basin on the side shown in FIG. 11.

At the upper end of the flow channel area is provided a feed trough opening 414 extending through the plate and communicating the basin 406 on the opposite side of the plate with the flow channel area 370. At the lower end of the flow channel area is provided an outlet trough opening 418, communicating the basin 412 on the opposite side of plate with the flow channel are 370.

On the floor 420 of the flow channel area, the top end 422 and bottom end 424 are downwardly sloped to the respective trough openings, with the floor otherwise being planar.

On this floor 420 of the flow channel area is provided a series of spaced-apart partitions 426, 428, 430, 432, 434, 436, and 438, which divide the flow channel area into a series of corresponding flow channels 440, 441, 442, 443, 444, 445, 446, and 447. The partitions are substantially the same height as bounding wall 374 and are substantially parallel to one another, whereby the respective channels 440–447 extend longitudinally between the liquid feed trough 416 and the liquid collection (outlet) trough 418.

It will be noted that while seven partitions are provided on the floor of the flow channel area in the plate of FIG. 11, only six partitions are positioned on the floor 197 of the flow channel area in the plate of FIG. 2. The purpose of such disparity in number of partitions is to enhance the support by the plates of the interposed filter element support. Thus, a staggered array of partitions is provided on the oppositely facing plates, whereby the rigidity and structural integrity of the overall assembly is enhanced. It will be appreciated that the number and placement of the partitions on filter plates of the present invention may be varied widely, depending on the specific application intended, within the broad practice of the invention.

In the corner regions of the plate shown in FIG. 11, depressions 450, 451, 452, and 453 are provided for mating with the corresponding locator pins 176, 174, 172, and 170 of the facing plate shown in FIG. 2. Such alignment structures may be varied, and other forms of alignment devices may be suitably alternatively be employed.

In the FIG. 11 plate, the inner wall 374 is formed with a depression 455 in its top surface. The depression accommodates the insertion thereinto of a suitable sealing gasket or other sealing means, to cooperatively mate the plate with a filter element support of the type shown in FIGS. 7–10, with leak-tight sealing of the flow channel volume therebetween.

Figure 12:
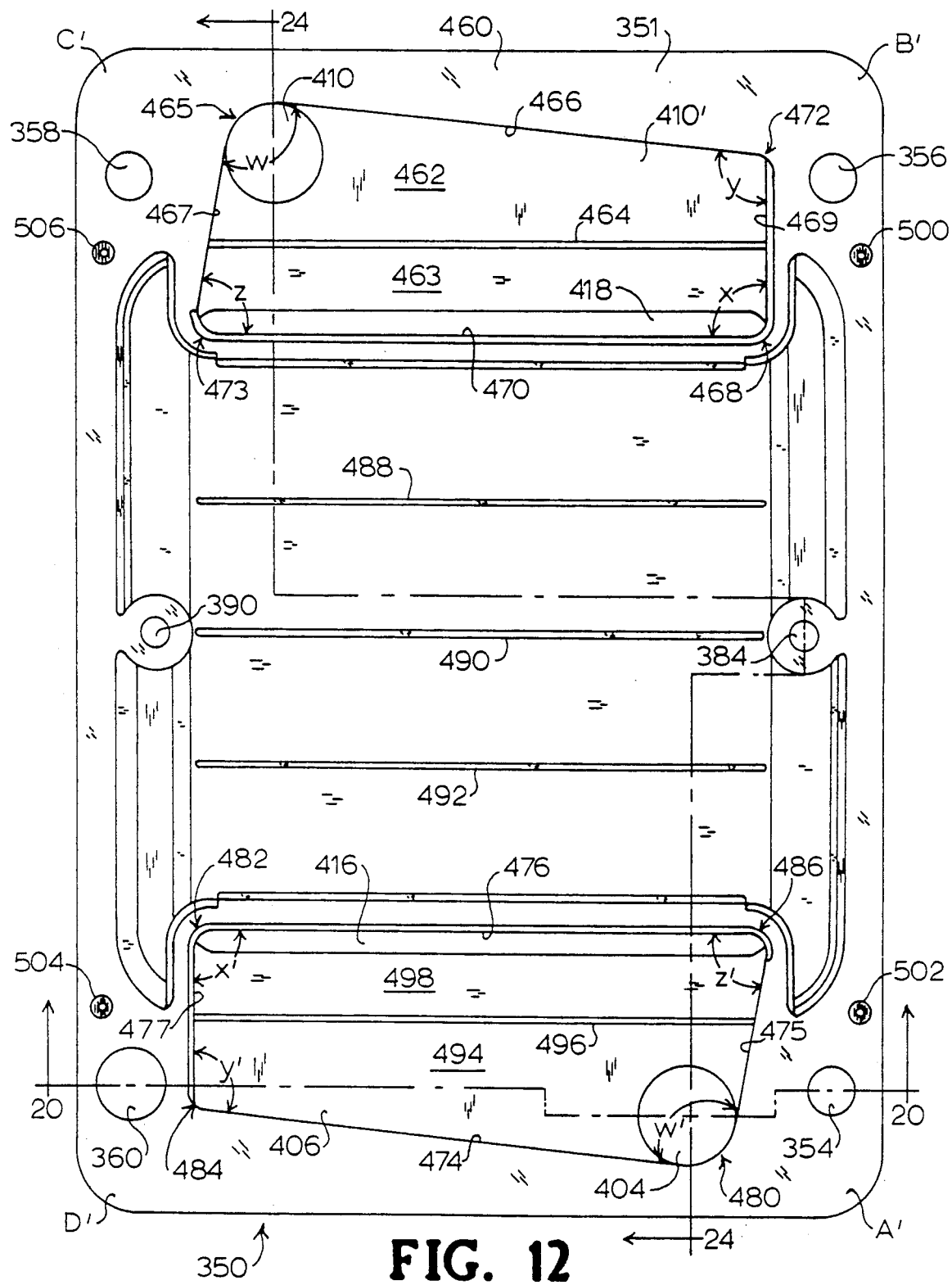
FIG. 12 is a bottom plan view of the filter plate of FIG. 11.

FIG. 12 is a plan view of the filter plate of FIG. 11, on the opposite side thereof, wherein all corresponding parts and elements are numbered identically to the same parts and elements in FIG. 11.

As shown, the plate body 351 has a main top surface 460 which is generally planar and generally rectangular in shape. In the ensuing discussion of the plate as shown in FIG. 12, the surface 460 will be referred to as the main top surface and all other elevations and depressions will be referenced thereto for ease of description, it being understood that the "top" surface of FIG. 12 is in fact the "bottom" surface of the plate as shown in FIG. 11, and vice-a-versa. Thus, for simplicity, each plate surface has been described as shown in the respective Figures, from the orientation of the viewer of these drawings, and consistent with the description of the corresponding filter plate in FIGS. 1 and 2.

At the upper end of the plate shown in FIG. 12 there is provided a liquid collection basin 410. The basin is formed as a depression in the main body 351 of the plate, relative to main top surface 460. The collection basin has a planar main floor portion 462 and a planar ridge surface 463 of higher elevation than the main floor portion 462 and joined with the main floor portion by sloping transition section 464.

The collection basin 410 has port opening 410 disposed at a first corner 465 thereof, where the side surfaces 466 and 467 of the basin intersect to define an included angle w therebetween. Diagonally opposite first corner 465 is a second corner 468 of the basin, where the bounding side walls 469 and 470 intersect, to define an included angle x therebetween. Basin side walls 467 and 469 intersect at a third corner 472 of the basin, defining an included angle y therebetween. The fourth corner 473 of the basin is formed by the intersection of side walls 467 and 470, defining an included angle z therebetween.

The feed basin 406 is correspondingly configured, with the respective side walls 474, 475, 476, and 477 defining included angles w', x', y', and z', at their respective intersections with one another at the corners 480, 482, 484, and 486.

On the main top surface 460 of the plate, in the central portion thereof corresponding to the flow channel area on the opposite side of the plate, there are provided a series of transversely extending parallel ridge elements 488, 490, and 492. These transversely extending ridges serve to rigidify and strengthen the plate so that the plate is not deformed under high pressure conditions in the flow channel volume formed by mating of the flow channel areas of adjacent facing plates in the stacked filter of the present invention.

In the illustrative filter plate embodiments of the invention, as shown in FIGS. 1, 2, 11, and 12, the quadrilateral-shaped liquid distribution basins may include an obtuse angle w of about 94°, a substantially right (90°) angle x, an obtuse angle y of about 96°, and an acute angle z of about 80° at the respective corners of the basin. In like manner, the filter plate embodiments of FIGS. 1, 2, 11, and 12 feature liquid collection basins of quadrilateral shape including corners characterized by angles w', x', y' and x', which are of corresponding values to angles w, x, y, and z of the liquid distribution basins of these plate embodiments, respectively.

Although the quadrilateral shape of the respective liquid distribution and collection basins may be widely varied in the broad practice of the present invention, as regards the specific values of the corner angles of such basins, the specific shape and angles shown in FIGS. 1 and 12 are most preferred to facilitate uniformity of flow path length for liquid across the entire areal extent of the respective basins and flow channel area, i.e., a generally uniform velocity profile of the fluid flowing longitudinally across the flow channel area of the plate.

Thus, apart from the above-described illustrative embodiment, it will be appreciated that the respective corner angles of the quadrilateral-shaped basins in the plate of the invention may be varied considerably, in accordance with the general ranges and values specified in Table I below.

TABLE I

Corner Angle Ranges and Values for Quadrilateral-Shaped Liquid Distribution and Collection Basins

| Basin Corner Angle | General Range and Values | Preferred Range and Values |
| --- | --- | --- |
| w, w' | about 60° to about 110° | about 90° to about 100° |
| x, x' | about 45° to about 90° | about 80° to about 90° |
| y, y' | about 70° to about 140° | about 80° to about 115° |
| z, z' | about 60° to about 90° | about 75° to about 90° |

In the basin 406, the main floor portion 494 is substantially planar and below the plane of the main top surface 460 of the plate, and is joined by a sloping transition section 496 with a plateau or ridge 498 which is of higher elevation than the main floor of the basin. The ridge 498 in turn is substantially planar and is intermediate in elevation between the floor portion 494 and the main top surface 460 of the plate.

In the corner regions of the plate shown in FIG. 12, there are provided keying elements 500, 502, 504, and 506. These keying elements enable the plate to be cooperatively aligned with an adjacent plate mated therewith in forming the stacked plate filter assembly of the invention.

FIG. 13 is a side elevation view of the plate shown in FIGS. 11 and 12, taken along line 13—13 of FIG. 11. FIG. 14 is a side elevation view of the plate of FIGS. 11 and 12, taken along line 14—14 of FIG. 11.

FIG. 15 is an edge elevation view of the filter plate, taken along line 15—15 of FIG. 11. FIG. 16 is an edge elevation view of the filter plate, taken along line 16—16 of FIG. 11. In all of these FIGS. 13-16, the parts and elements of the plate are numbered correspondingly with respect to FIGS. 11 and 12.

Figure 17:
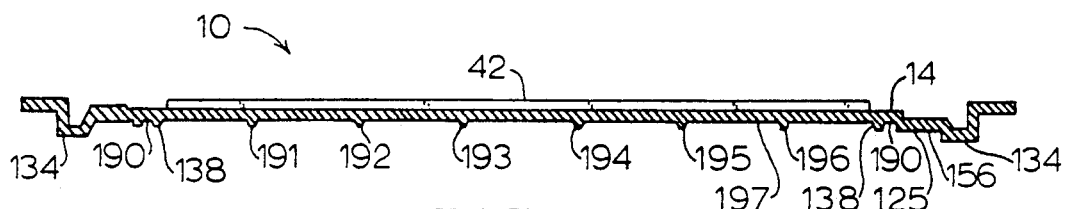
FIG. 17 is a sectional elevation view of the FIG. 2 plate, taken along line 17—17 thereof.

FIG. 17 is a sectional view, in elevation, of the FIG. 2 filter plate, taken along line 17—17 thereof, showing the transversely extending rib 42 on the opposite side surface 14 from that shown in FIG. 2. The main surface 125 features the outer wall 134 extending upwardly therefrom and circumscribing the flow channel area 197, with the inner circumscribing wall 138 featuring groove 190 for insertion thereinto of a sealing gasket (not shown). On the right-hand side of the cross-section shown in FIG. 17, the inner wall 138 is adjacent the ridge 156 extending from the inner wall to the outer wall 134.

On the main flow channel area floor 197 are provided the series of transversely spaced-apart partitions 191, 192, 193, 194, 195, and 196, which divide the flow channel area into a series of longitudinally extending, transversely spaced-apart flow channels, bounded by the respective partitions as shown.

Figure 18:
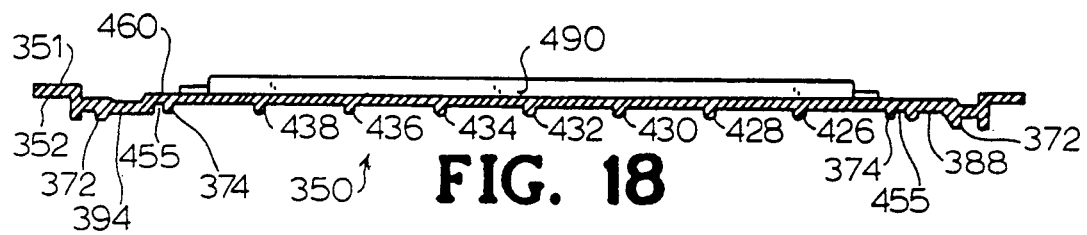
FIG. 18 is a sectional elevation view of the FIG. 11 plate, taken along line 18—18 thereof.

FIG. 18 is a sectional elevation view of the FIG. 11 plate, taken along line 18—18 thereof. The plate 350 shown in this view comprises a plate body 351 having a main surface 460 on which is disposed a transversely extending rib 490, and on the opposite main surface 352 of which is provided a series of partitions 426, 428, 430, 432, 434, 436, and 438 demarcating flow channels in the flow channel area of the plate. As shown, the flow channel area comprising the partitions is bounded at the margins of the plate by inner circumscribing wall 374 having groove 455 therein accommodating the insertion thereinto of a sealing gasket. The flow channel area is additionally circumscribed at the outer periphery of the plate by an outer wall 372 of greater height than the innerwall 374. Between the circumscribing walls 374 and 372 on the left-hand side of the plate in the view shown in FIG. 18, there is provided a ridge 394, and on the right-hand side of the plate as shown in such view, there is provided a longitudinally extending leg 388 of the L-shaped section of the plate.

Figure 19:
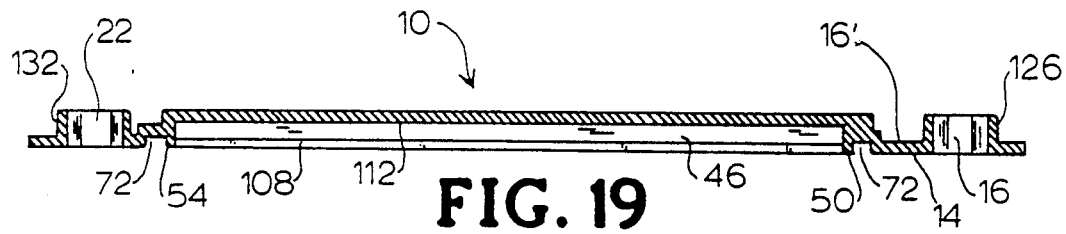
FIG. 19 is a sectional elevation view of the FIG. 1 plate, taken along line 19—19 thereof.

FIG. 19 is a sectional elevation view of the FIG. 1 plate, taken along line 19—19 thereof. As shown in such sectional view, the plate 10 has a first main surface 14 in which is provided the basin 46 as bounded by side walls 50 and 54. The basin floor 112 as shown is substantially planar, as is the main surface of ridge 108 (see also FIG. 1). At the respective side margins of the plate are provided rod mounting opening 16, surrounded by collar 126, and opening 22, surrounded by collar 132. A groove 72 is provided about the periphery of the basin 46 to accommodate insertion thereinto of a suitable sealing gasket (not shown).

Figure 20:
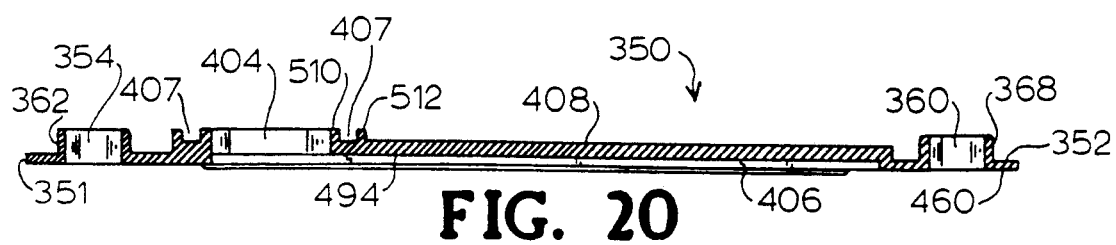
FIG. 20 is a sectional elevation view of the filter plate of FIG. 12, taken along line 20—20 thereof.

FIG. 20 is a sectional elevation view of the filter plate of FIG. 12, taken along line 20—20 thereof.

As shown in this view, the plate 350 comprises a main plate body 351 with a first main surface 352 and a second main surface 460. At the side margins of the plate are provided rod alignment opening 360, surrounded by collar 368, and opening 354, surrounded by collar 362. Liquid port opening 404 is circumscribed by respective inner wall 510 and outer wall 512, defining a groove 407 therebetween for insertion of a sealing gasket thereinto.

On main surface 460 of the plate, there is formed basin 406 having a substantially planar floor 494. The basin is disposed in flow communication with the port opening 404, with the basin forming the surface portion 408 on the main surface 352 of the plate.

Figure 21:
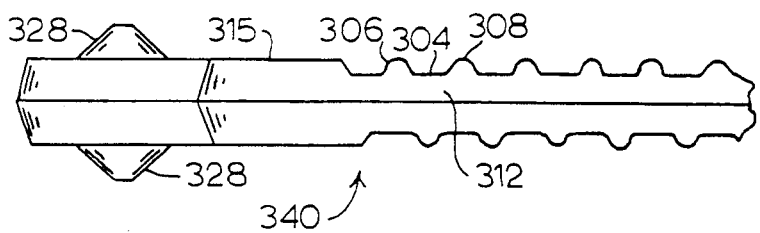
FIG. 21 is an enlarged edge elevation view of a portion of the filter element support shown in FIG. 10.

FIG. 21 is an enlarged edge elevation view of a portion of the filter element support shown in FIG. 10, showing the details of construction thereof. The support 340 comprises a side margin 315 having substantially planar top and bottom surfaces which are provided on a rearward corner portion thereof with frustoconical protrusions 326 and 328, to facilitate alignment and positioning of the support between two adjacent oppositely facing filter plates having corresponding depressions receiving the frustoconical protrusions on their surfaces mating with the filter element support.

The filter element support is characterized by a series of transversely spaced-apart ridges 306 and 308, between which are provided corresponding grooves 304. These ridges and grooves run lengthwise of the plate to each respective end edge thereof.

FIG. 22 is a sectional elevational view of the FIG. 1 plate, taken along line 22—22 thereof. As shown, the plate 10 is provided at the center of the plate with an opening 24 extending therethrough and bounded by radially spaced-apart walls 26 and 28 defining a groove 30 therebetween for insertion thereinto of a suitable sealing gasket (not shown). Transversely adjacent to the opening 24 in this view are ridges 40 and 44 on the upper main surface of the plate. At the right-hand end of the plate the port opening 44 extends through the plate and communicates with a basin 46 having a main floor portion 112 communicating with an upper ridge portion 108. The basin is circumscribed by a groove 72 into which a suitable sealing gasket (not shown) may be disposed for sealing of the plate against an opposedly mounted plate when employed in a stacked plate filter.

At the left-hand end of the plate in the view shown in FIG. 22, there is provided a corresponding basin 80 having a main floor portion 120 and an upper ridge portion 116. The basin is circumscribed by a groove 102 accommodating a sealing gasket (not shown). The basin communicates with the port opening 76 which extends through the plate.

On the underside of the plate as shown in FIG. 22, the flow channel area 136 is bounded by an inner circumscribing wall 138 having a groove 190 therein accommodating a sealing gasket (not shown).

At the right-hand end of the plate shown in FIG. 22, the trough opening 40 extends through the plate and communicates the basin 46 with the flow channel area 136 on the opposite side of the plate. In like manner, the trough opening 102, at the left-hand part of the plate as shown, communicates the basin 80 with the flow channel area 136.

FIG. 23 is an enlarged sectional elevation view of a portion of the plate shown in FIG. 22, with all parts and elements therein correspondingly numbered to FIG. 22.

FIG. 24 is a sectional elevation view of the FIG. 12 filter plate, taken along line 24—24 thereof. The plate 350 as shown in this view features a central opening 384 extending through the plate, adjacent to which, on the upper surface 460 of the plate, are transversely extending ribs 488 and 492. On the lower main surface of the plate as shown in this view, the port opening 410 at the right-hand portion of the plate extends through the plate and is circumferentially bounded by a groove 407 accommodating insertion thereinto of a suitable gasket element. At the left-hand side of the plate as shown, the port opening 404 extends to the plate and is circumferentially bounded by groove 407' accommodating a corresponding sealing gasket. The port opening 410 is in communication with the basin 410' on the upper surface of the plate. Correspondingly, port opening 404 communicates with the basin 406 at the other end of the plate.

Liquid trough opening 418 extends to the plate and communicates the basin 410' with the flow channel area 370 on the lower side of the plate. In like manner, trough opening 416 extends through the plate and communicates the basin 406 at the other end of the plate with the flow channel area 370. The flow channel area is circumscribed by an inner wall 374 having a groove 455 in the top surface thereof to accommodate a gasket element. The flow channel area is also circumscribed by a second, outer wall 372 which has a groove 520 therein to accommodate a sealing gasket.

Figure 25:
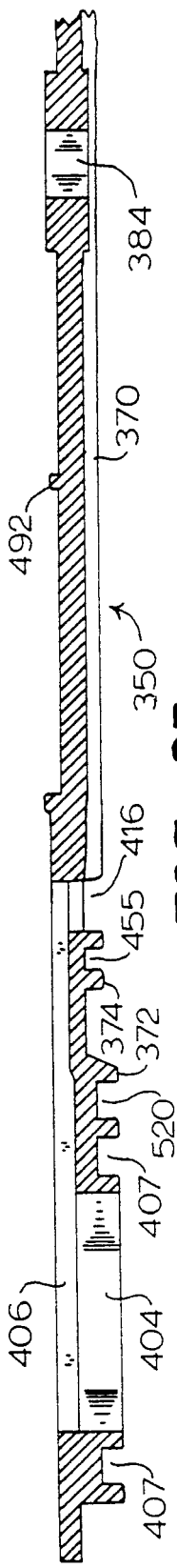
FIG. 25 is an enlarged portion of the sectional elevation view shown in FIG. 24.

FIG. 25 is an enlarged sectional elevation view of a portion of FIG. 24, wherein all parts and features are correspondingly numbered to FIG. 24.

Figure 26:
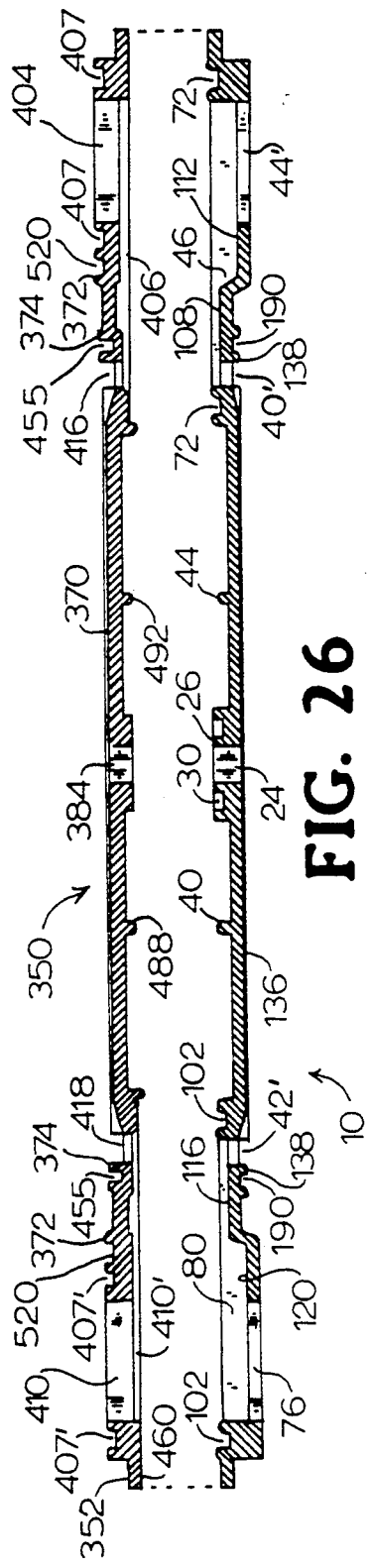
FIG. 26 is a sectional elevation view of complementarily matable filter plates corresponding to the respective plates shown in FIGS. 22 and 24, in proximate matable relationship to one another.

FIG. 26 is a sectional elevation view of complementarily matable filter plates corresponding to the respective filter plates shown in FIGS. 22 and 24, in proximate matable relationship to one another. In these drawings, the parts and elements of the respective plates have been numbered correspondingly to FIGS. 22 and 24.

Figure 27:
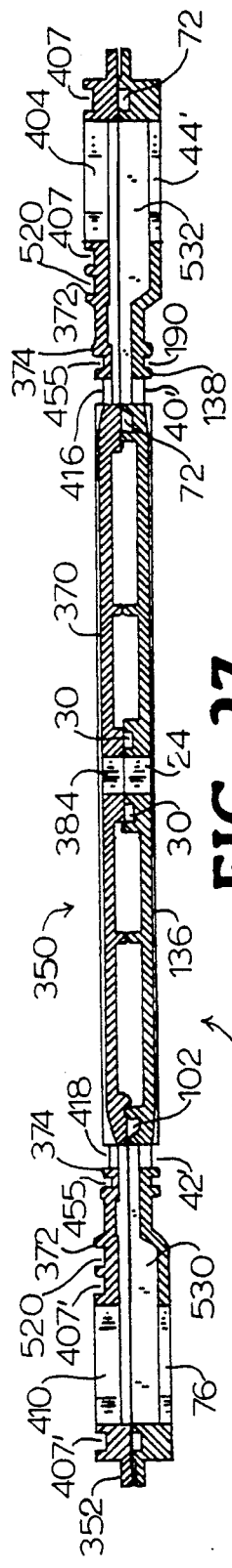
FIG. 27 is a sectional elevation view of the respective filter plates shown in FIG. 26, as opposedly mated with one another to form a paired, stacked plate unit.

FIG. 27 is a sectional elevation view of the respective filter plates shown in FIG. 26, as opposedly mated with one another to form a paired, stacked plate unit. The parts and elements in FIG. 27 are numbered correspondingly with respect to FIG. 26. FIG. 27 shows the plates forming an interior basin volume 530 communicating with the respective trough openings 418 and 42, to supply liquid to the flow channel areas 370 and 136, respectively. After longitudinally traversing the respective flow channel areas 370 and 136, the liquid then flows via plate openings 416 and 40 into the interior basin volume 532 at the opposite end of the plate from basin 530. In this manner, the liquid is introduced via the feed port comprising port openings 410 and 72, and is withdrawn from the stacked array by a discharge port comprising discharge openings 404 and 44, at the diagonally opposite end of the stacked plate assembly from the inlet port.

Figure 28:
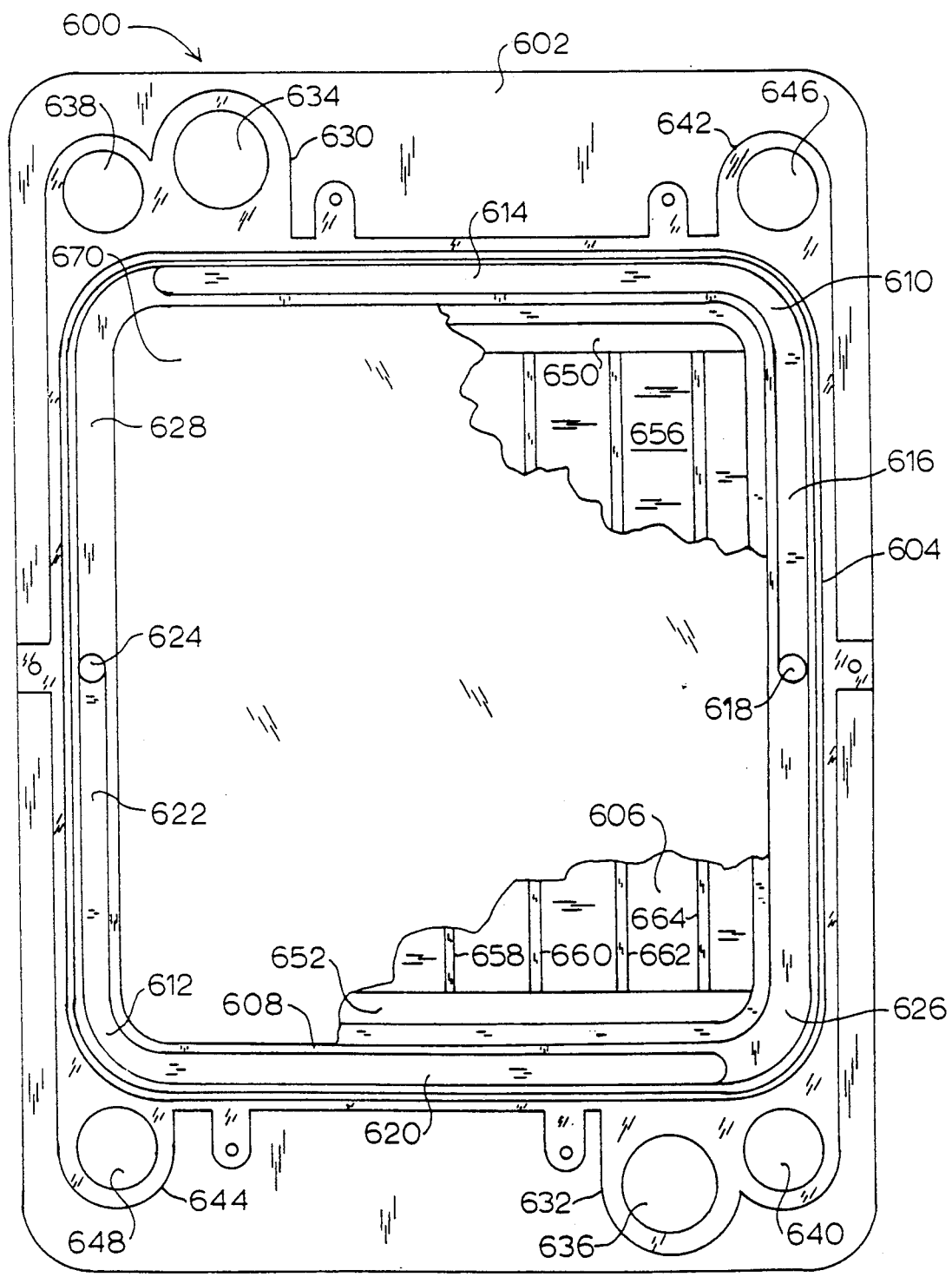
FIG. 28 is a top plan view of a filter plate according to still another embodiment of the present invention.

FIG. 28 is a top plan view of a filter plate 600 according to still another embodiment of the present invention. The filter plate 600 has a generally rectangular and generally planar shape with a main top surface 602 on which a first upwardly extending wall 604 circumscribingly bound a flow channel area 606 of generally rectangular shape. A second upwardly extending wall 608 is provided, which is interior to and of lesser height than the first bounding wall 604. The second wall is in spaced relation to the first wall along diagonally opposed L-shaped peripheral sections 610 and 612.

The L-shaped peripheral section 610 comprises a leg 614 extending transversely across the flow channel area for a major portion of the width thereof, and a leg 616 extending longitudinally for a portion of the length of the flow channel area and communicating at its extremity with an opening 618 extending through the plate. Diagonally opposite L-shaped peripheral section 610 is peripheral section 612, comprising a leg 620 extending transversely across the flow channel area for a major portion of the width thereof, and a leg 622 extending longitudinally for a portion of the length of the flow channel area and communicating at the extremity of the leg with an opening 624 extending through the plate. By such configuration, the L-shape peripheral sections define flow passages which may be used for example to drain permeate from the peripheral sections through the openings 618 and 624 for discharge from the filter plate.

The peripheral portions of the flow channel area not comprising such L-shaped sections comprise ridges 626 and 628 between the respective circumscribing walls 608 and 604.

The outer circumscribing wall 604 includes diagonally outwardly extending sections 630 and 632, which enclose respective liquid port openings 634 and 636, and rod mounting openings 638 and 640. In the remaining corners of the plate, the outer circumscribing wall 604 has comprises additional outwardly extending portions 642 and 644, which respectively enclose rod mounting openings 646 and 648.

The upper end of the flow channel area 606 comprises a liquid trough opening 650 extending through the plate, and a corresponding liquid trough opening 652 is provided at the lower end of the flow channel area 606.

Intermediate the respective liquid trough openings 650 and 652, the flow channel area 606 comprises a main central and generally planar floor 656. Extending upwardly from the floor 656 are a plurality of partitions 658, 660, 662, and 664, which divide the flow channel area into corresponding channels which extend longitudinally between the respective liquid trough openings 650 and 652.

In the filter plate embodiment shown in FIG. 28, a filter sheet 670 is bonded at its perimeter to the innner circumscribing wall 608, by any suitable means and/or method of attachment, including adhesive bonding, ultrasonic welding, fusion bonding, solvent welding, etc. The filter sheet 670 may be formed of any suitable material of construction, as for example polysulfone of a selected permeability a appropriate to the filtration operation which is to be conducted using the plate.

Thus, the filter plate of FIG. 28 features the filter sheet element joined to the plate itself, rather than being bonded to the filter element support, as in the previously described embodiments of the invention. The plate configuration of FIG. 28 may for example be of preferred configuration, as opposed to the previously described plate embodiments, when the permeate has a tendency to clog or otherwise occlude the permeate passages in the filter element support. In such instances, the filter element support can be readily disengaged from the adjacent pair of plates between which it is interposed, and subjected to the requisite cleaning operations to regenerate same for further use. Such configuration thus achieves a major advantage over the previously described plate embodiments in such cloggingprone applications, which would otherwise require a filter element support having filter sheets attached thereto to be disassembled, which is tediuos, time-consuming, and costly, or else discarded, which is economically disadvantageous.

Generally, in the plate configuration of FIG. 28, it is desired to secure the filter sheet 670 to the inner circumscribing wall 608 around the entire peripheral extent of the filter sheet, so that the flow channel is sealed by the filter sheet.

Figure 29:
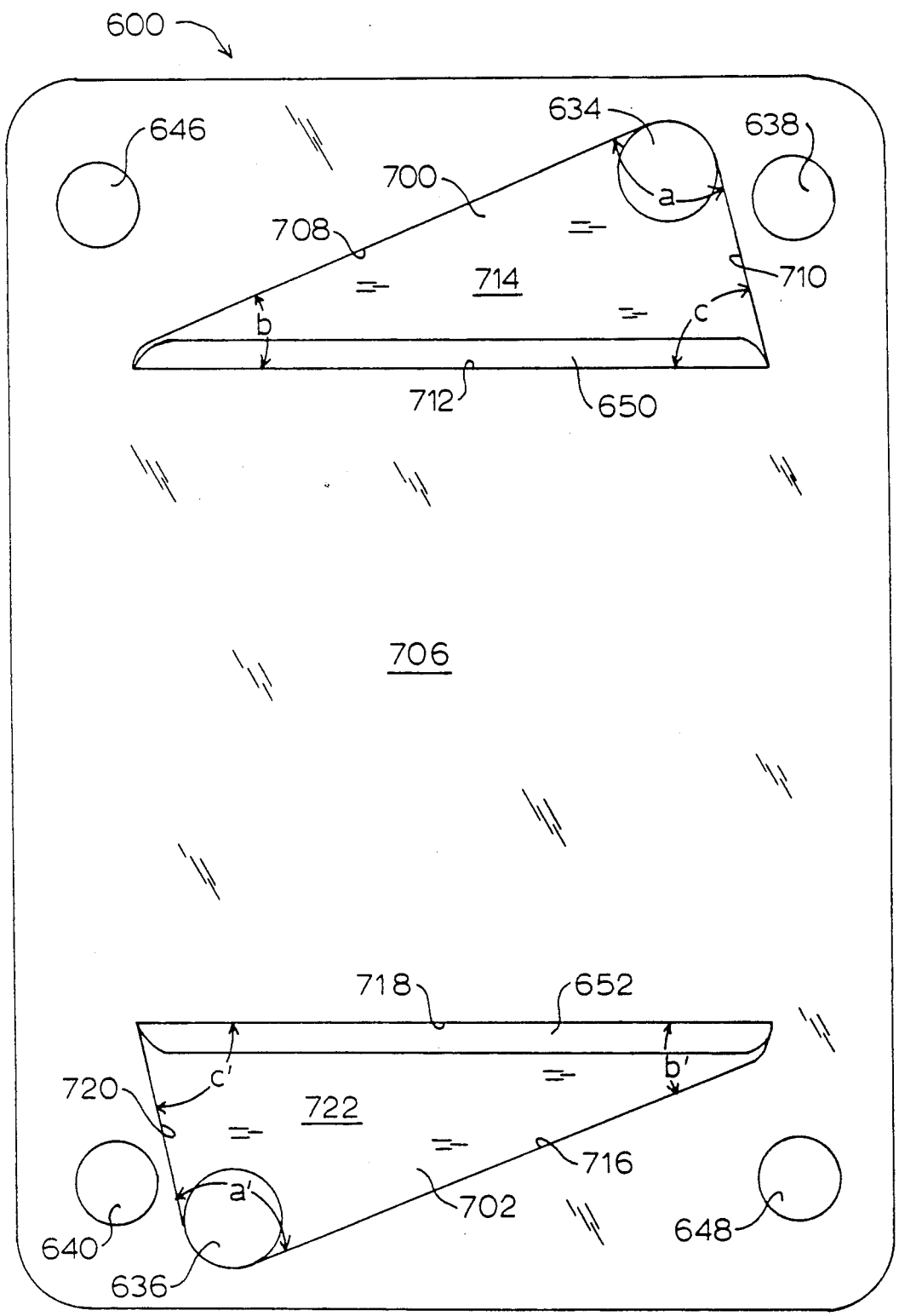
FIG. 29 is a bottom plan view of the filter plate of FIG. 28, showing the details of construction of the liquid distribution and liquid collection basins thereof.

FIG. 29 is a bottom plan view of the filter plate of FIG. 28, showing the details of construction of the liquid distribution and liquid collection basins thereof. In FIG. 29, all parts and elements are numbered correspondingly with respect to FIG. 28.

As shown, the plate 600 of FIG. 29 is provided with a liquid distribution basin 700, and a liquid collection basin 702, which are of triangular shape. The liquid distribution basin 700 is formed as a depression in the main bottom surface 706 of the plate.

The liquid distribution basin is bounded by side walls 708, 710, and 712, defining respective included angles a, b, and c at the apices of the basin. The basin has a generally planar floor 714, and the liquid inlet port opening 634 is disposed at the corner of the basin at which the side walls 708 and 710 define the include angle a.

Correspondingly, the liquid collection basin 702 is bounded by side walls 716, 718, and 720. This basin has generally planar floor 722 which is of a selected depth relative to the main bottom surface 706 of the plate. The liquid discharge port opening 636 is disposed at the corner of the triangular basin formed by the intersection of side walls 716 and 720, such side walls defining an included angle a' therebetween. The included angle b' is formed by the intersection of side walls 716 and 718, and the included angle c' is formed by the intersection of side walls 718 and 720.

While the angles a, b, and c of the liquid distribution basin 700 and the angles a', b', and c' of the liquid collection basin 702 may be varied widely in the broad practice of the present invention, it generally is desired that angles a and a' be in the range of from about 60° to about 120°, that angles b and b' be in the range of from about 15° to about 45°, and that angles c and c' be in the range of from about 45° to about 75°. Thus, in the filter plate shown in FIGS. 28 and 29, the liquid inlet trough 650 communicates the liquid distribution basin 700 with the flow channel area 606 of the filter plate. Correspondingly, the liquid collection trough 652 communicates the flow channel area 606 of the plate with the liquid collection basin 702. In this manner, liquid to be filtered is introduced to the plate through the inlet port opening 634 and is distributed by the distribution basin 700 to the distribution trough 650 for distributed flow across the flow channel area 606 of the plate. At the opposite end of the flow channel area, the filtered liquid enters the liquid collection trough 652 and flows to the liquid collection basin 702 for discharge from the plate through the liquid discharge port opening 636.

The filter plates of the present invention may be fabricated in any suitable manner, including machining, casting, injection molding, etc., the specific method of fabrication depending on the material of construction and the desired end use. For example, for high temperature filtration applications, polysulfone is a preferred material of construction for the filter plates, interposed filter element support, and filter sheets. Accordingly, when polysulfone is utilized as the material of construction, injection molding may suitably be employed as the method of fabrication.

In injection molding generally, it is difficult to push a resin through a series of small mold cavity volumes of widely varying thickness, to ensure adequate filling of the mold and production of the desired article. In this respect, the filter plates and filter element support of the present invention are characterized by a remarkably uniform thickness across the full areal extent thereof, facilitating injection molding. For example, the filter element support may have a thickness on the order of about 110 to about 130 mils (0.11–0.13 inch). As shown in the enlarged cross section of the filter element support in FIG. 21, the respective ridges 306 and 308 on the opposite sides of the support are staggered with respect to one another, to ensure a relatively constant cross section to facilitate injection molding. In the filter support element of the foregoing dimensional characteristic, the ridges may be transversely spaced apart by a distance on the order of 0.092 inch, and the ridge height may be on the order of 0.02 inch.

Correspondingly, the filter plate may have a thickness which averages about 0.080 inch across its full areal extent, with only minor deviations from such thickness in specific localized areas of the plate structure.

Although polysulfone has been indicated as a preferred injection molding material, and additionally is highly suitable for elevated temperature applications, the filter plates may be suitable formed with any other injection moldable resin or material which is productive of a plate with the desired physical and performance characteristics. Examples include polyvinyl chloride, polyvinylidene chloride, polyethylene, polytetrafluoroethylene, etc.

Figure 30:
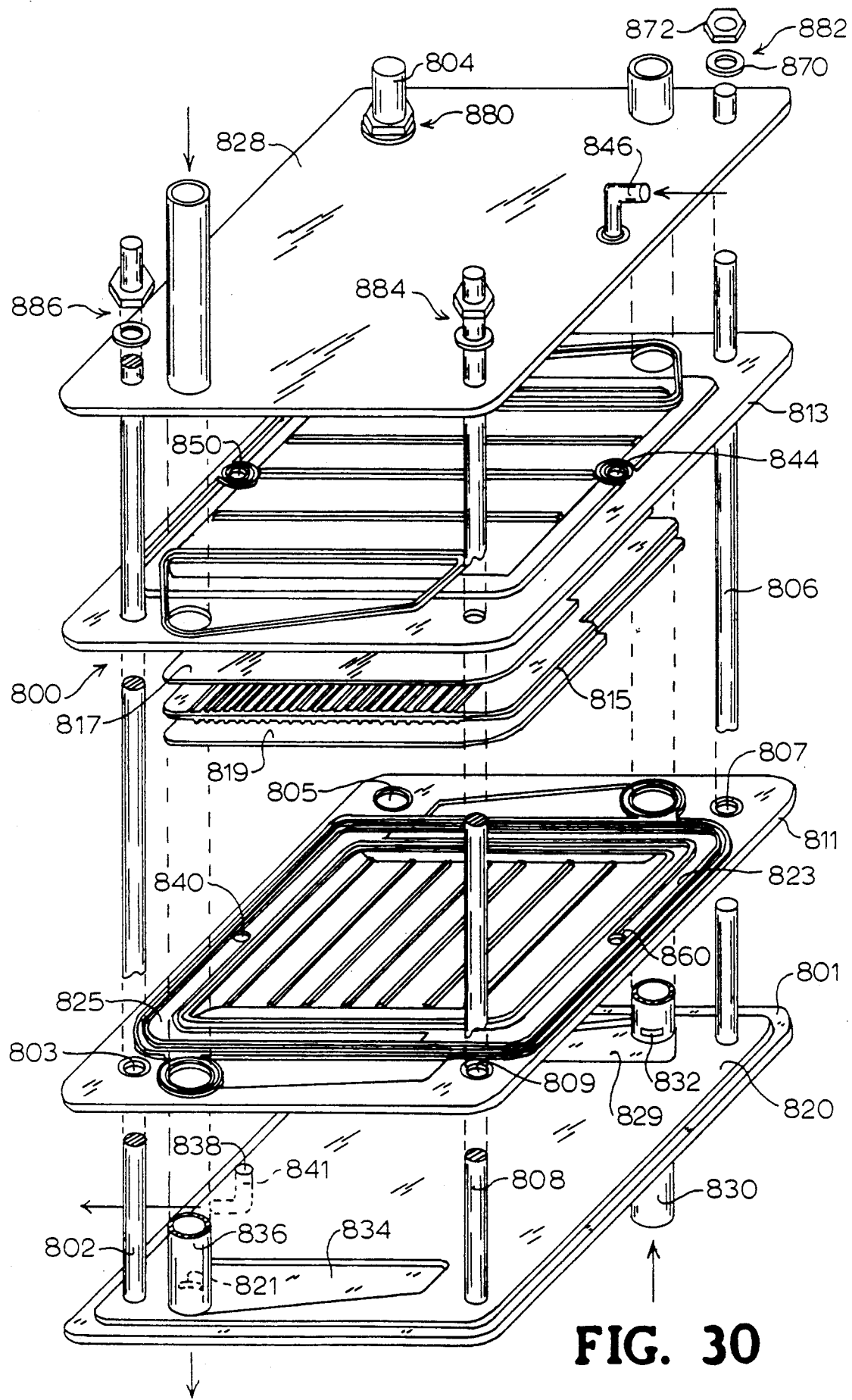
FIG. 30 is an exploded perspective view of a stacked plate filter assembly according to one embodiment of the present invention, showing the details of construction thereof.

FIG. 30 is an exploded perspective view of a stacked plate filter assembly 800 according to one embodiment of the present invention, showing the details of construction thereof.

This stacked plate filter 800 comprises a base including a mounting plate 801 having vertically upwardly extending rods 802, 804, 806, and 808 at its respective corner portions as shown. Each of the rods 802, 806, and 808 are of the same diameter, while the fourth rod 804 is of larger diameter, to provide a plate orientation keying structure, which will ensure that the constituent plates of the filter assembly are assembled in the proper orientation, since the corresponding rod mounting openings 803, 807, and 809 in the plates, e.g., plate 811, are of the same diameter, accommodating the smaller diameter rods, while the fourth rod mounting opening 805 is of larger diameter, to accommodate rod 804. Thus, by providing a rod of larger diameter, and forming the plates 811 and 813 with correspondingly shaped openings, the proper registration of the plate openings with the proper rods is assured, resulting in correct orientation of the respective stacked filter plates in the array.

It will be appreciated from the foregoing that any other plate orientation registration device may be employed to ensure the correct positioning of the successive stacked filter plates on the mounting plate 801. For example, the plates may be formed with a notch in one of their side edges, so that all successive plates are oriented with their successive notches superposed with respect to one another. Alternatively, the plate itself may be embossed, etched, or otherwise manufactured with an orientational device, e.g., a raised protrusion in the shape of an arrow, to indicate the correct orientation of the filter plates when stacked on the mounting plate 801. Filter plates 811 and 813 are of the general type previously described hereinabove, with filter plate 81 generally corresponding to the filter plate shown in FIG. 11, and filter plate 813 generally corresponding to the plate shown in FIG. 1, with respect to the faces visible in the perspective view of FIG. 30.

A filter element support 815, mated with filter sheets 817 and 819 on its respective top and bottom faces, is interposed between the opposed filter plates 811 and 813, which are oriented in inverted facing relationship to one another, so that the respective plates form an enclosed liquid flow channel containing the filter element (filter element support 815, and filter sheets 817 and 819).

Between the lower filter plate 811 and mounting plate 801, there is provided a sealing gasket 820 which is equipped with openings to accommodate its positioning over the respective rods 802, 804, 806, and 808, so that the gasket seals the bottom surface of the lower plate 811.

As shown, the sealing gasket 820 is provided with a transversely elongate opening 829, accommodating the liquid inlet conduit 830 and the liquid distribution basin of the filter plate 811 positioned thereagainst, and in communication with the liquid feed opening 832.

Similarly, the gasket 820 features a transversely elongate opening 834, accommodating the liquid withdrawal conduit 836 and the liquid collection basin of the filter plate 811, and in liquid flow communication with liquid outlet opening 821.

Gasket 820 also is provided with an opening 838 communicating with opening 840 of plate 811 and a corresponding opening in the mounting plate 801 to which is joined the secondary fluid outlet conduit 841.

The gasket 820 may be formed of any suitable material which is sealingly effective in the stacked plate filter assembly, such as for example silicone, Buna-N, or EPDM rubber materials, or flexible polymeric materials commerically available under the trademarks Viton ®, Calrez ®, and Teflon ®.

While the stacked plate assembly shown in FIG. 30 is illustrated with only two filter plates according to the present invention, it will be appreciated that the stacked plate filter may be readily assembled with any selected number of plates, arranged in appropriate pairs, and operated as desired to provide filtration, and/or primary and secondary fluid contacting operations.

For example, the stacked plate assembly of FIG. 30 may be arranged for mass transfer contacting of a primary fluid and a secondary fluid. The primary fluid is introduced in liquid inlet conduit 830, flowed across the flow channels of the constituent filter plates to a liquid outlet, and discharged from the system in liquid outlet conduit 836. The secondary fluid is introduced into the stacked assembly via secondary fluid inlet conduit 846, and flowed through the filter element grooved passages bounded by the filter element support and the adjacent filter sheet, from the L-shaped channels 823 of the paired plates in proximity to the secondary fluid inlet 844, to the L-shaped channels 825 diagonally opposite the L-shaped channels 823, for discharge of secondary fluid from the stacked assembly in secondary fluid outlet conduit 841, via the opening 840 in plate 811.

As an alternative to the stacked plate assembly shown in FIG. 14, constructed for primary and secondary fluid contacting, the assembly may be constructed for normal filtration operation, with permeate being withdrawn from the set of L-shaped channels 825 in communication with the plate openings 840 and 850, via outlet conduit 841, and with permeate being withdrawn from the other set of L-shaped channels 823, in communication with plate openings 860 and 844, via conduit 846, so that permeate is withdrawn from the conduit 846 opposite to the direction indicated by the arrow.

Alternatively, there may be provided corresponding openings in gasket 820 and mounting plate 801, communicating with openings 860 and 844 of the respective lower and upper filter plates, to withdraw permeate through a conduit joined to the mounting plate 801, analogous to withdrawal conduit 841.

The stacked filter array thus is built up by stacking plates in respective facing pairs until a predetermined height of stacked plates is obtained, followed by placement over the stacked assembly of the top end plate 828. Each of the respective rods 802, 804, 806, and 808 is threaded on its upper outer surface for mating with complementary mechanical fasteners such as the washer and nut assemblies 880, 882, 884, and 886, comprising washers 870 and nuts 872.

It will be apparent from the foregoing that the respective sections of stacked plates may be variously joined in fluid flow communication with one another, in series, to form stacked filter "trains" whose constituent sections may be employed to carry out a number of unit operations on an influent or feed material, such as concentrating (dewatering), washing, dialyzing, desalting, etc.

For example, a stacked filter train of series-connected sections may be employed in a culturing system of the type disclosed and claimed in my copending patent applications U.S. Ser. No. 06/936,486 filed Nov. 26, 1986, and U.S. Ser. No. 07/207,655 filed June 21, 1988, the disclosures of which hereby are incorporated by reference, in applications such as the production in vitro of human immunodeficiency virus (HIV) on cellular or synthetic substrates. In such HIV production application, a first stacked plate section could be employed to concentrate HIV, a second section could be utilized to add media to or withdraw media from the system, all without withdrawing any virus, such as may otherwise present a risk of immunosuppressive infection. Thus, a closed system virus culturing arrangement is provided, which is highly advantageous not only for the production of HIV but also the culturing or other processing of pathogenic as well as non-pathogenic bacterial, viral, and yeast species.

While the invention has been described with reference to specific illustrative embodiments, it will be apparent that there are other variations, modifications, and embodiments possible within the broad scope of the invention, and that all such variations, modifications, and embodiments are to be regarded as being within the spirit and scope of the invention.

What is claimed is:

1. A filter plate comprising:
   (a) a generally rectangular and generally planar shape with main top and bottom surfaces;
   (b) a first wall extending upwardly from said main top surface and circumscribingly bounding a flow channel area of generally rectangular shape thereon;
   (c) a second wall on said main top surface extending upwardly therefrom, said second wall being interior to and of lesser height than said first wall and in spaced relationship to the first wall along diagonally opposed L-shaped peripheral sections of the flow channel area thereby defining an L-shaped channel therebetween;
   (d) each L-shaped peripheral section comprising said L-shaped channel which comprises a leg extending transversely across the flow channel area for a major portion of the width thereof, and a leg extending longitudinally for a portion of the length of the flow channel area and communicating at its extremity with an opening extending through the plate, with peripheral portions of the flow channel area not comprising said L-shaped sections comprising ridges extending between the first and second walls;
   (e) an inlet port opening in the filter plate at a first end thereof, extending through the plate, and interiorly positioned in a polymodal-shaped distribution basin on the main bottom surface of the plate, said distribution basin being bounded by generally linear side edges defining corners of the basin at respective intersections of the side edges;
   (f) an inlet trough opening extending through said plate and transversely across a major portion of the width of said flow channel area and along a first side edge of said distribution basin, such that said inlet trough opening communicates said distribution basin on the main bottom surface of the plate with said flow channel area on the main top surface of the plate;
   (g) an outlet port opening in the plate at a second end thereof extending through the plate, and interiorly positioned in a polygonal-shaped collection basin on the main bottom surface of the plate, said collection basin being bounded by generally linear side edges defining corners of the collection basin at respective intersections of the side edges thereof;
   (h) an outlet trough opening extending through the plate and transversely across a major portion of the width of said flow channel area nd along a first side edge of said collection basin, such that said outlet trough opening communicates said collection basin on the main bottom surface of the plate with said flow channel area on the main top surface of the plate; and
   (i) a plurality of transversely spaced-apart partitions extending upwardly from the floor of the flow channel area between the inlet trough opening and the outlet through opening, said partitions being of substantially the same height as the second wall and substantially parallel to one another to define a series of channels between the partitions, extending longitudinally between the inlet trough opening and the outlet through opening.

2. A filter plate according to claim 1, wherein the distribution basin and collection basin each have quadrilateral shape, and wherein each basin comprises:
   said port opening being disposed at a first said corner and the side edges intersecting at said first corner defining a first included angle w therebetween of from about 60° to about 100°;
   a second corner diagonally opposite said first corner, and the side edges intersecting at said second corner defining a second include angle x therebetween of from about 45° to about 90°;
   a third corner transversely adjacent said first corner and longitudinally adjacent said second corner, with the side edges intersecting at said third corner defining a third includes angle y therebetween of from about 70° to about 135°;
   a fourth corner longitudinally adjacent said first corner and transversely adjacent said third corner, with side edges intersecting at said fourth corner defining a fourth angle z therebetween of from about 60° to about 90°; and
   the side edge extending transversely between said second and fourth corners also bounding the associated trough opening extending through said plate and communicating said basin with said flow channel area.

3. A filter plate according to claim 1, comprising triangular-shaped distribution and collection basins at respective ends of the filter plate, each such basin including a transversely extending side edge bounding the associated trough opening extending through the plate and communicating the basin with the flow channel area, wherein the basins are bounded by substantially linear side edges defining corners of the basin at respective intersections of the side edges, and each basin comprising:

the port opening being disposed at a first said corner and the side edges intersecting at said first corner defining an included angle a therebetween of from about 60° to about 120°;

a second corner adjacent the associated trough opening and the side edges intersecting at said second corner defining an included angle b therebetween of from about 15° to about 45°;

a third corner transversely opposite said second corner, with the side edges intersecting at said third corner defining an included angle c therebetween of from about 45° to about 75°.

4. A stacked plate filter comprising filter plates provided in invertedly positioned symmetrical facing pairs, wherein each pair of filter plates forms an enclosed liquid flow channel, with a filter element disposed in each flow channel;

each of said filter plates comprising (a) a generally rectangular and generally planar shape with main top and bottom surfaces;

(b) a first wall extending upwardly from said main top surface and circumscribingly bounding a flow channel area of generally rectangular shape thereon;

(c) a second wall on said main top surface extending upwardly therefrom, said second wall being interior to and of lesser height than said first wall and in spaced relation to the first wall along diagonally opposed L-shaped peripheral sections of the flow channel area thereby defining an L-shaped channel therebetween;

(d) each L-shaped peripheral section comprising said L-shaped channel which comprises a leg extending transversely across the flow channel area for a major portion of the width thereof, and a leg extending longitudinally for a portion of the length of the flow channel area and communicating at its extremity with an opening extending through the plate, with peripheral portions of the flow channel area not comprising said L-shaped sections comprising ridges extending between the first and second walls;

(e) an inlet port opening in the filter plate at a first end thereof, extending through the plate, the interiorly positioned in a polygonal-shaped distribution basin on the main bottom surface of the plate, said distribution basin being bounded by generally linear side edges defining corners of the basin at respective intersections of the side edges;

(f) an inlet trough opening extending through said plate and transversely across a major portion of the width of said flow channel area and along a first side edges of said distribution basin, such that said inlet trough opening communicates said distribution basin on the main bottom surface of the plate with said flow channel area on the main top surface of the plate;

(g) an outlet port opening in the plate at a second end thereof extending through the plate, and interiorly positioned in a polygonal-shaped collection basin on the main bottom surface of the plate, said collection basin being bounded by generally linear side edges defining corners of the collection basin at respective intersections of the side edges thereof;

(h) an outlet trough opening extending through the plate and transversely across a major portion of the width of said flow channel area and along a first side edge of said collection basin, such that said outlet trough opening communicates said collection basin on the main bottom surface of the plate with said flow channel area on the main top surface of the plate; and (i) a plurality of transversely spaced-apart partitions extending upwardly from the floor of the flow channel area between the inlet trough opening and the outlet through opening, said partitions being of substantially the same height as the second wall and substantially parallel to one another to define a series of channels between the partitions, extending longitudinally between the inlet trough opening and the outlet trough opening.

5. A stacked plate filter according to claim 4, wherein said filter element comprises a filter element support of generally planar and non-perforate character, with opposed, longitudinally extending marginal flanges, said filter element support having main top and bottom surfaces, characterized by a series of transversely spaced-apart ridges which extend longitudinally of the support along its full longitudinal extent, and with the margins of the filter element support being devoid of such ridges.

6. A stacked plate filter according to claim 5, wherein the filter element comprises filter sheets reposed on main top and bottom surfaces of said filter element support.

* * * * *